United States Patent [19]

Hagiwara et al.

[11] Patent Number: 5,298,252

[45] Date of Patent: *Mar. 29, 1994

[54] ANTIMICROBIAL COMPOSITION HAVING RESISTANCE TO HEAT AND WEATHERS

[75] Inventors: Zenji Hagiwara, Shiga; Masao Okubo, Hyogo, both of Japan

[73] Assignees: Hagiwara Research Corp., Kusatsu; Japan Electronic Materials Corporation, Amagasaki, both of Japan

[*] Notice: The portion of the term of this patent subsequent to Sep. 14, 2010, has been disclaimed.

[21] Appl. No.: 751,969

[22] Filed: Aug. 29, 1991

[30] Foreign Application Priority Data

Mar. 22, 1991 [JP] Japan .................. 3-058956

[51] Int. Cl.$^5$ .......... A01N 25/08; B32B 5/16
[52] U.S. Cl. .................. 424/409; 556/10; 424/630; 424/652; 424/653; 424/641; 424/644; 424/489; 424/497; 424/684; 428/403; 428/198
[58] Field of Search .......... 424/78.1, 409, 489, 424/684, 630, 652, 653, 644, 641, 497; 556/10; 428/403, 198

[56] References Cited

U.S. PATENT DOCUMENTS

| | | | |
|---|---|---|---|
| 3,923,969 | 12/1975 | Boukal et al. | 424/468 |
| 4,006,175 | 2/1977 | Tormin et al. | 556/10 |
| 4,525,410 | 6/1985 | Hagiwara et al. | 428/198 |
| 4,959,268 | 9/1990 | Hagiwara et al. | 428/403 |

FOREIGN PATENT DOCUMENTS

| | | |
|---|---|---|
| 116865 | 1/1984 | European Pat. Off. . |
| 235431 | 8/1986 | European Pat. Off. . |
| 251783 | 7/1987 | European Pat. Off. . |
| 253663 | 7/1987 | European Pat. Off. . |

OTHER PUBLICATIONS

World Patent Index Week 9051, Nov. 8, 1900 for JPA-2273591 (English Language abstract).

*Primary Examiner*—Peter F. Kulkosky
*Attorney, Agent, or Firm*—Venable, Baetjer, Howard & Civiletti

[57] ABSTRACT

A silica gel based heat-resistant and weatherproof antimicrobial composition having an aluminosilicate layer on the surfaces of pores in the silica gel as substituted by silver and an optional antimicrobial metal, said composition containing ion-exchangeable metals that are chiefly an alkali metal and that are present in an amount of up to 2.57 mmol per gram of said composition on an anhydrous basis.

5 Claims, No Drawings

ANTIMICROBIAL COMPOSITION HAVING RESISTANCE TO HEAT AND WEATHERS

RELATED APPLICATION

The present application is closely related to copending application, Ser. No. 662,040 filed Feb. 28, 1991 and entitled "Antimicrobial Compositions".

This invention relates to a novel antimicrobial composition and a process for producing it. More particularly, this invention relates to a heat-resistant and weatherproof antimicrobial composition that is based on a silica gel and that has an aluminosilicate layer which is substituted by antimicrobial metals in such a way that ion-exchangeable metals are contained in the composition in an amount that does not exceed a specified value. The invention also relates to a process for producing such a novel antimicrobial composition.

A great number of organic antibacterial and antifungal agents are known in the art, as exemplified by PCP (pentachlorophenol), PCMX (p-chloro-m-xylenol), Preventol A-3 [N-(trichloromethylthio)phthalimide], Preventol A-4 [N-N-dimethyl-N-phenyl-(N'-fluoromethylthio)sulfamide], organotin compounds, Vinyzene (Bentron Co.), TBZ [2-(4-thiazolyl)benzimidazole, Merck & Co., Inc.] and OBPA (10,10-oxybisphenolarsine). However, most of these organic antimicrobial agents have comparatively narrow antimicrobial spectra and cannot be used in a broad range of applications but their use is limited to certain bacteria and fungi. As a further problem, many of those organic antimicrobial agents are not highly heat-resistant and when they are compounded into polymers in an attempt to make them resistant to microorganisms or to kill them, the agents may undergo either degradation or evaporation loss, which can not only cause time-dependent change in the physical properties and color of the polymers but also reduce their antimicrobial or microbicidal effects. In addition, most of the organic antimicrobial agents have been found to be so toxic that they are not desirable from a safety viewpoint.

In order to solve those problems of the known organic antimicrobial agents, one of the inventors of the present invention proposed the use of inorganic antimicrobial agents that were based on crystalline aluminosilicates (zeolite) or amorphous aluminosilicates and that had not only broad antimicrobial spectra but also high safety feature (Japanese Patent Publication Nos. 54013/1988, 32254/1989 and 46620/1990, and Japanese Patent Public Disclosure No. 181002/1985).

Those inorganic antimicrobial agents have broad antimicrobial spectra and hence they are suitable for use in a broad range of applications. In addition, they have excellent antimicrobial capabilities and their antimicrobial or microbicidal effects will be sustained for a prolonged period. However, those inorganic antimicrobial agents have one problem that remains yet to be solved, namely, the low resistance to heat and weathers (light) which is ascribable to the structure of the matrix, say, antimicrobial zeolite. Under the circumstances, it has been necessary to improve the weatherproofness of antimicrobial zeolites under illumination with light or there has been a need to prevent or reduce the time-dependent change in the color of antimicrobial or microbicidal polymers prepared by mixing the antimicrobial zeolite with various polymers. To this end, the use of various additives such as a stabilizer, a weatherproofing agent, an antioxidant, a modifying agent, an optical brightening agent, a UV (ultraviolet) absorber and a pigment in the manufacture of those antimicrobial or microbicidal polymers is currently practiced. Further, using those additives in combination with compounds of divalent metals such as alkaline earth metals is also attempted to enhance the heat resistance of the antimicrobial zeolite or the polymers that contain it. However, these approaches are by no means the best solution to the aforementioned problems of the prior art and there are many problems that remain to be solved. It is therefore necessary to develop a new approach for solving the pending problems.

The present invention provides a novel inorganic antimicrobial agent that has an entirely different matrix structure from the known inorganic antimicrobial agents in order to overcome the low heat resistance and weatherproofness of those known products such as antimicrobial zeolites.

The present inventors found that the heat resistance and weatherproofness of an inorganic antimicrobial composition could be improved by reducing the contents of ion-exchangeable metals, typically, alkali metals in the composition. The present invention has been accomplished on the basis of this finding.

The present invention provides a heat-resistant and weatherproof antimicrobial composition that is based on a silica gel having an aluminosilicate layer on the surfaces of pores in the silica gel as substituted by silver and optional other antimicrobial metals, said composition containing ion-exchangeable metals in amounts not exceeding specified values.

The antimicrobial composition of the present invention has a greater antimicrobial or microbicidal action than known antimicrobial compositions and is capable of killing common bacteria and fungi at faster speeds. Further, the composition has not only high heat resistance and weatherproofness but also good dispersibility.

The invention as recited in appended claim 1 relates to a silica gel based heat-resistant and weatherproof antimicrobial composition that has an aluminosilicate layer on the surfaces of pores in silica gel that is substituted by silver and optional other antimicrobial metals, said composition containing ion-exchange metals, typically, alkali metals in amounts not exceeding 2.57 mmol, preferably not exceeding 2.0 mmol, per gram of the composition on an anhydrous basis.

The ion-exchangeable alkali metal to be contained in the composition of the present invention is preferably selected from the group consisting of lithium, sodium, potassium and mixtures thereof. The antimicrobial composition of the present invention (-,an be prepared by performing ion-exchange with a solution of mixed salts containing a plurality of antimicrobial metal ions so as to achieve substitution by a plurality of antimicrobial metals. Alternatively, a silver-containing antimicrobial composition may be used as a mixture with a separately prepared antimicrobial composition that contains another antimicrobial metal.

The composition of the present invention thus substituted by antimicrobial metals desirably has a pore volume of at least 0.3 $cm^3/g$ and a specific surface area of at least 100 $m^2/g$, preferably up to 500 $m^2/g$, more preferably up to 400 $m^2/g$, on an anhydrous basis. If the composition having such physical property data is used, the rate of reaction with bacteria and fungi is further increased to achieve higher mortality on those microorganisms. Specific surface area measurements were conducted by the BET method and this applies in the following description unless otherwise noted.

The degree of substitution by antimicrobial metals is preferably at least 0.04 equivalent fraction. The "degree of substitution by antimicrobial metals" is expressed by the number of equivalents of a certain antimicrobial metal divided by the total exchange capacity of the antimicrobial composition containing said antimicrobial metal. If two or more antimicrobial metals are to be used, their total amount is preferably at least 0.04 equivalent fraction. The degree of substitution by antimicrobial metals is preferably not more than 0.95 equivalent fraction.

Silver is the essential antimicrobial metal to be contained in the composition of the present invention. Other antimicrobial metals may optionally be used in combination with silver. Such optional antimicrobial metals are selected from the group consisting of copper, zinc, mercury, tin, lead, bismuth, cadmium and chromium.

The antimicrobial composition of the present invention may be mixed with a polymer to prepare an antimicrobial polymer composition leaving high weatherproofness. Such a polymer composition preferably contains 0.01-25 wt % of the antimicrobial composition.

The antimicrobial composition of the present invention can be prepared by the following method. First, a silica gel is treated with an alkali solution and an aluminate solution to yield a reaction product that has a non-antimicrobial aluminosilicate layer on the active surfaces of pores in the silica gel, which layer contains ion-exchangeable metals, typically alkali metals, in amounts not exceeding 2.6 mmol per gram of the product on an anhydrous basis. Subsequently, the ion-exchangeable metals in the non-antimicrobial layer are ion-exchanged with silver and optional other antimicrobial metals, thereby producing a silica gel based antimicrobial composition having high resistance to heat and weathers.

The silica gel serving as the matrix is in no way limited to any particular shape. While it may be in any form selected from among a powder, granules, a pulverized part and a shaped part (e.g., beads and pellets), fine shapes are preferred from the viewpoint of reactivity in the subsequent chemical treatment. Further, in consideration of the physical properties of silica gel, it desirably has a porous structure in which an infinite number of pores have developed in the interior to provide large values of pore size and specific surface area (SSA). The pore volume (P.V.) of the silica gel is preferably at least 0.3 cm³/g (on an anhydrous basis), more preferably at least 0.4 cm³/g. The pore size of the silica gel is desirably as large as possible, and the preferred value is at least 50 Å, more preferably at least 70 Å. The SSA of the silica gel is desirably at least 100 m²/g on an anhydrous basis, with values of at least 200 m²/g (on an anhydrous basis) being more advantageous.

The alkali solution with which the silica gel is to be treated may be a solution of an alkali metal hydroxide such as NAOH, KOII or LIOH. Tile treatment may be performed at either ambient or elevated temperatures with the pH being held in the range of 8.4–13.5.

The aluminate solution with which the silica gel is to be treated may be a solution of an alkali metal aluminate such as $NaAlO_2$, $KAlO_2$ or $LiAlO_2$. Also usable is a solution of an aluminate obtained by reacting an aluminum compound with excess strong alkali.

By performing the chemical treatment described above, silica ($SiO_2$) that is dominant on the surfaces of pores in the silica gel react with the alkali or aluminate solution and, as a result, a non-antimicrobial layer that is substantially composed of an aluminosilicate containing ion-exchangeable alkali metals as a chief component will form, mostly on the surfaces of pores in the silica gel. In this case, the total amount of ion-exchangeable alkali metals in the non-antimicrobial layer is preferably adjusted to be no more than 2.6 mmols per gram of the non-antimicrobial composition in an anhydrous state.

The amount of alkali metals to be present in the treated silica is adjustable depending upon the concentration of the aluminate, the reaction time and the reaction temperature and by properly selecting those conditions, the amount of alkali metals can be adjusted to no more than 2.6 mmols.

The non-antimicrobial layer formed on the surfaces of pores in the silica gel has an extremely stable bond with the matrix silica gel and hence will hardly separate from the latter. This non-antimicrobial layer is composed of an amorphous and/or crystalline aluminosilicate. When the above-described reaction for the formation of the non-antimicrobial layer is performed at ambient temperature, said layer is mostly amorphous; if, on the other hand, the reaction is performed at elevated temperatures, for example, at 60°-70° C., two types of aluminosilicate, amorphous and crystalline, will form as a mixture. The non-antimicrobial layer is represented by the following general chemical formula:

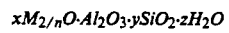

$$xM_{2/n}O \cdot Al_2O_3 \cdot ySiO_2 \cdot zH_2O$$

where x and y represent the numbers of molecules of the metal oxide and silicon dioxide, respectively; M is an ionexchangeable metal; n is the atomic valence of M; and z is the number of molecules of water. M is an ion-exchangeable metal, typically an alkali metal such as Li, Na or K, and permits the presence of other metals such as monovalent $NH_4^+$ (ammonium ion), divalent Mg, Ca, Sr, Mn, Ni or Co, or Fe (divalent or trivalent). The thickness and composition of the non-antimicrobial layer to be formed on the surfaces of pores in the silica gel may be properly adjusted by controlling various factors including the physical properties of the starting material for silica gel, the amount of its use, the concentration of alkali, the amount of addition of aluminate, as well as the reaction temperature and time.

The intermediate reaction product that is obtained by performing the chemical treatment described above and that has the non-antimicrobial layer held on the surfaces of pores in the matrix silica gel is subsequently washed with water to remove the excess alkali salts present in the solid phase.

As already mentioned, the non-antimicrobial layer has such a stable bond to the matrix silica gel that sodium, aluminum, silica and any other components of the layer will not dissolve away even if it is subjected to washing with water. In the next step, the intermediate reaction product is subjected to ion-exchange with antimicrobial (or microbicidal) metal ions to form an antimicrobial (or microbicidal) layer. To this end, the intermediate reaction product having the non-antimicrobial layer is treated with a silver ion containing solution having a microbicidal action or a neutral or slightly acidic solution containing both silver ion and at least one metal ion selected from the group of antimicrobial metals consisting of copper, zinc, mercury, tin, lead, bismuth, cadmium and chromium. Examples of the silver ion containing solution are solutions of $AgNO_3$, $AgClO_4$ and silver acetate. The solution that contains both silver ion and other antimicrobial metal ions may be exemplified by solutions containing $AgNO_3$, $AgClO_4$, silver acetate, etc. in combination with antimicrobial metal containing salts such as $Cu(NO_3)_2$, $Zn(NO_3)_2$, $ZnSO_4$, $SnSO_4$, $Zn(ClO_4)_2$, $Cu(ClO_4)_2$, $Cd(ClO_4)_2$, zinc acetate, copper tartrate and cadmium citrate. Using such solutions that contain the antimicrobial silver ion ($Ag^+$) either alone or in combination with other antimicrobial metal ions, the ion-exchangeable metals (M) in the aluminosilicate layer are subjected to ion-exchange at ambient or elevated temperatures, whereby a predetermined amount of the antimicrobial metal or metals are fixed to the aluminosilicate layer by ionic bonding so as to form an antimicrobial layer. As a result of this step, the silica gel based antimicrobial composition of the present invention is prepared.

The solution containing one or more antimicrobial metal ions to be used in the ion-exchange treatment may also contain monovalent, divalent or polyvalent metal ions having no antimicrobial activity. Even if major amounts of antimicrobial metal ions and minor amounts of non-antimicrobial metal ions are ionically bonded to the aluminosilicate layer in the ion-exchange step for forming the antimicrobial layer, the presence of the latter metal ions will not be deleterious to the effectiveness of the antimicrobial or microbicidal layer and, hence, the presence of both antimicrobial and non-antimicrobial metal ions is permissible in the ion-exchange treatment. The degree of substitution by antimicrobial metal ions is governed by various factors including the concentration or composition of salt solutions containing those metal ions, the amount of concomitant non-antimicrobial salts, if any, as well as the reaction time and temperature for the ion-exchange treatment. By proper selection of these conditions, the amount of antimicrobial metals present in the antimicrobial layer can be easily controlled in such a way that they are contained in the antimicrobial composition in an anhydrous state in amounts of the preferred range of 0.04–0.95 equivalent fraction. It is also easy in the present invention to insure that sodium and other alkali metals that can affect the heat resistance or weatherproofness of the claimed composition is adjusted to be no more than 2.57 mmol per gram of the composition on an anhydrous basis.

After washing off the excess antimicrobial salts and any other impurities that are present in the solid phase, the silica gel based antimicrobial composition of the present invention is dried at temperatures near 100° C. If a specific use of the composition is such that further reduction in the water content is necessary, it may be dried under vacuum or dehydration may be performed with the heating temperature elevated to 200°–350° C. If there is a need to make a fine powder of the composition, it may be reduced to fine particles with a suitable grinder.

The silica gel material having the physical data listed above is very porous and the surfaces of pores in it are very active to provide high reactivity. By performing the above-described chemical treatment on the silica gel having this physical nature, a non-antimicrobial aluminosilicate layer is formed on the surfaces of pores in the matrix and, thereafter, the aforementioned antimicrobial (or microbicidal) metals are retained stably on the non-antimicrobial layer by ion-exchange, whereby the said layer is rendered antimicrobial to form an antimicrobial (or microbicidal) layer. The use of the silica gel material under consideration offers the advantage that various chemical species and metal ions that take part in reaction will diffuse rapidly enough to permit the intended chemical reaction to proceed smoothly on the surfaces of pores in the silica gel. The use of the silica gel material having the physical data listed above has another advantage: silver and other antimicrobial metals present in the finally obtained antimicrobial composition of the present invention are distributed substantially uniformly in a preferred way in the aluminosilicate layer formed on the surfaces of pores in the silica gel, so antimicrobial or microbicidal metal ions formed as a result of dissociation of those metals will diffuse rapidly through pores to insure that those antimicrobial or microbicidal metal ions will contact bacteria or fungi over a sufficiently large area to inhibit their growth or kill them effectively. The surface of the antimicrobial composition of the present invention has a stronger bacterial or fungal adsorbing power than known antimicrobial zeolites. Hence, this antimicrobial composition exhibits an excellent antimicrobial or microbicidal action.

The antimicrobial composition of the present invention can be produced by a process that comprises chemically treating a silica gel material having the above-described characteristics with an alkali solution and an aluminate solution so as to form a non-antimicrobial layer on the surfaces of pores in the silica gel matrix and then rendering this layer antimicrobial to form an antimicrobial layer.

The pores in the silica gel based antimicrobial composition of the present invention are larger than those in known aluminosilicate based antimicrobial agents. Hence, microbicidal metal ions formed as a result of dissociation of the composition will readily diffuse through the pores to have easy access to microorganisms. On the other hand, the pores is known aluminosilicate based antimicrobial compositions, such as antimicrobial zeolites, are so small in size that microbicidal metal ions formed as a result of dissociation will diffuse very slowly and sometimes fail to have contact with microorganisms. Hence even if the apparent specific surface area is increased by using porous aluminosilicate particles, the area over which a microbicidal metal makes effective contact with microorganisms will not increase so much as to enhance their antimicrobial performance to a desired level. This is because the effectiveness of the microbicidal metal present on the surface of the matrix is reduced by "dead spaces" where it is unable to have contact with microorganisms.

The antimicrobial composition of the present invention does not have this problem and all microbicidal metals that are present on the surface of the matrix work effectively by contacting microorganisms.

Further, the silica gel matrix is covered with an aluminosilicate substituted by a microbicidal metal, so the amount of "wasted" microbicidal metal which is occluded within the matrix and hence prevented from contact with microorganisms is substantially reduced.

Because of these two factors, the "effective availability" of the microbicidal metal, namely, the proportion of the metal used that is occupied by the metal present on the surface, is markedly increased to insure that the composition of the present invention need be used in a smaller amount to exhibit satisfactory antimicrobial performance.

The silica gel based antimicrobial composition of the present invention is characterized by having much higher heat resistance and weatherproofness (lightfastness) than known organic or inorganic antimicrobial agents. The antimicrobial composition of the present invention is thermally very stable, even in the temperature range of 100°-500° C. which is commonly adopted in preparing antimicrobial polymers by kneading said composition into polymers under heating. The structure of the composition remains stable even if it is heated to a temperature close to 500° C. As a further advantage, the antimicrobial or microbicidal capability of the composition will not deteriorate at all over the temperature range of 100°-500° C.

The probable reason for the high heat resistance of the antimicrobial composition of the present invention would be as follows. The antimicrobial (or microbicidal) layer formed on the surfaces of an infinite number of pores in the matrix silica gel of the composition has a uniform distribution of antimicrobial metals which are covered by excess silica present in the three-dimensional skeletal structure of the silica gel and this would contribute to the marked enhancement of the heat resistance and weatherproofness of the composition.

As set forth hereinabove, the amount of alkali metals present in the non-antimicrobial layer is adjusted to be no more than 2.6 mmol per gram of the composition and this condition must be satisfied in order to enhance not only the heat resistance but also the weatherproofness of the finally obtained antimicrobial composition by minimizing the contents of alkali metals. If the finally obtained antimicrobial composition contains an excessive amount of alkali metals, alkalies and other hydrolyzates of alkali metal ions will cause adverse effects on the physical properties of the antimicrobial composition. To take a silver-containing antimicrobial composition as an example, if it is irradiated, in the presence of a high alkali metal content, with light of varying energy, its weatherproofness will deteriorate upon increasing the exposure, eventually causing a change in color or other properties with time. In order to avoid this problem, the content of alkali metal in the antimicrobial composition is limited to be no more than 2.6 mmol per gram of the composition. If the intermediate composition supporting the non-antimicrobial layer that contains alkali metals in amounts not exceeding 2.6 mmol per gram of the final composition is processed by the method of the present invention to prepare the final antimicrobial composition, the amount of alkali metals present in the antimicrobial layer is so small that their adverse effects on weatherproofness will be effectively blocked. Further, when the antimicrobial composition thus prepared which has low contents of alkali metals supported on the antimicrobial layer is mixed with various polymers and heated, the resulting antimicrobial-polymer compositions have weatherproofness that is remarkably improved over that of conventional inorganic antimicrobial agents. As a matter of fact, the time-dependent changes occurring in those polymer compositions upon exposure to light decreased to practically insignificant levels as evidenced by the $\Delta E_{ab}*$ data given later in this specification. Therefore, if antimicrobial polymers are to be prepared using the antimicrobial agent of the present invention, the additives that have to be incorporated when preparing antimicrobial polymers using known inorganic antimicrobial agents such as antimicrobial zeolites need not be used at all or need only to be used in very small amounts depending on the type of polymer with which the agent is to be mixed.

As will be demonstrated later in the Examples, the antimicrobial composition of the present invention exhibits surprisingly high levels of antimicrobial or microbicidal action that have not been attainable by known inorganic antimicrobial agents and it is capable of killing bacteria and fungi at extremely high speeds. In order for the composition of the present invention to exhibit comparable efficacy to the conventional antimicrobial agents, it need be used in a smaller amount (see the data of Antimicrobial Evaluation Test).

The present invention also provides an antimicrobial polymer composition having high weatherproofness that is chiefly composed of a polymer and the above-described heat-resistant and weatherproof antimicrobial composition. The antimicrobial composition of the present invention is preferably contained in an amount of 0.01-25 wt % of the polymer composition.

Both halogenated and non-halogenated organic polymers may be used in preparing the antimicrobial polymer composition of the present invention. Non-halogenated organic polymers may be synthetic or semi-synthetic and include, but not limited to, the following:

Thermoplastic synthetic polymers such as polyethylene, polypropylene, polystyrene, polyamide, polyesters, polyvinyl alcohol, polycarbonates, polyacetals, ABS resins, acrylic resins, fluorine resins, polyurethane elastomers and polyester elastomers; thermosetting synthetic polymers such as phenolic resins, urea resins, melamine resins, unsaturated polyester resins, epoxy resins and urethane resins; and regenerated or semi-synthetic polymers such as rayon, cuprammonium rayon, cellulose monoacetate, cellulose diacetate and cellulose triacetate. If a strong antimicrobial and/or microbicidal effect is necessary, the polymer composition is preferably foamed or otherwise shaped into a net, a fiber, etc. Preferred from this viewpoint are organic or fiber-forming polymers such as synthetic polymers exemplified by nylon 6, nylon 66, polyvinyl alcohol, polyethylene terephthalate, polybutylene terephthalate, polyacrylonitrile, polyethylene, polypropylene and copolymers thereof, and regenerated or semi-synthetic polymers exemplified by rayon, cuprammonium rayon, cellulose monoacetate, cellulose diacetate and cellulose triacetate. Halogenated organic polymers that can be used in the present invention also are not limited to any particular kinds and may be exemplified by polyvinyl chloride and polyvinylidene chloride.

The time at which the silica gel based antimicrobial composition is added to the polymer and the method by which it is added are not limited in any particular way in the present invention. For example, the antimicrobial composition may be mixed with a starting monomer and the mixture is then polymerized. In another method, the composition may be mixed with a reaction intermediate and the mixture is then polymerized. Alternatively, the composition may be mixed with the completed polymer. If desired, the silica gel based antimicrobial is mixed with polymer pellets or a master batch is prepared from a polymer containing said composition and the mixture or master batch is shaped to a desired form. In still another method, the antimicrobial composition is mixed with a molding dope, for example, a spinning solution. The procedure of these methods is hereinafter referred to simply as "mixing the silica gel based antimicrobial composition with a polymer or adding it to the polymer". A suitable method may be adopted taking into account the characteristics of the polymer used and process conditions. In ordinary cases, the silica gel based composition is desirably mixed with the polymer just before molding. However, in order to insure more efficient dispersion of the silica gel based antimicrobial composition, it may be mixed with a monomer. Prior to addition to a polymer, the anti-microbial composition may advantageously be dried or heat-treated as already mentioned hereinabove. When a predetermined amount of the antimicrobial composition is to be added to a polymer, the atmosphere (e.g. an oxidizing atmosphere such as the air or an inert gas atmosphere such as $N_2$ or $CO_2$), the temperature for mixing or the mixing time may be held at preferred conditions in accordance with the specific characteristics of the polymer used. The silica gel based antimicrobial composition is preferably used in an amount of 0.01-25 wt % of the total weight of the polymer composition. If the content of the silica gel based composition is less than 0.01 wt % of the total weight of the polymer composition, the antimicrobial and/or microbicidal activity of the polymer composition is often unsatisfactory against common bacteria and fungi. If the content of the silica gel based composition is more than 25 wt % of the total weight of the polymer composition, the antimicrobial and/or microbicidal activity of the resulting polymer composition is saturated and any further addition of the silica gel based composition will not contribute to an improved antimicrobial and/or microbicidal action. Furthermore, excessive addition of the silica gel based composition has the potential to deteriorate the physical properties of the finally obtained polymer composition.

The particle size of the silica gel based antimicrobial composition that is advantageously used to produce the antimicrobial polymer composition of the present invention is discussed below. While there is no particular limitation on the particle size of said composition, there is of course a preferred range depending on the specific use of the final product. For example, particles of the antimicrobial composition with sizes of 20-100 mesh can be used for mixing with the polymer but in order to insure more uniform dispersion in the polymer, smaller particles, for example, those having sizes of 200-300 mesh or much finer particles with sizes of from several microns to less than a hundred microns, may be used.

The particle size of the antimicrobial composition may be adjusted by selecting the particle size of the starting silica gel or by pulverizing the prepared silica gel based antimicrobial composition with a mill that is selected as appropriate for a specific purpose. When the antimicrobial polymer composition of the present invention is a shaped part leaving a certain thickness, for example, in the case where it is to be applied to various types of containers, pipes, granules of filaments of large denier, the silica gel based antimicrobial composition may have particle sizes of up to less than a hundred to less than a thousand microns or even more. If, on the other hand, the polymer composition is to be shaped into fibers of fine denier or thin films, the particle size of the silica gel based antimicrobial composition is desirably small. For example, in the case of manufacturing fibers for apparel, particle sizes of not more than 7 microns are preferred.

In addition to the silica gel based antimicrobial composition, the antimicrobial polymer composition of the present invention may contain other ingredients that are commonly used in the art. Examples of such secondary ingredients include: polymerization catalysts, stabilizers, weathering (lightfast) agents, compounding agents, antioxidants, activators, matting agents, foaming agents, flame retardants, modifiers, brighteners, pigments (colorants), inorganic or organic fillers, various plasticizers, and lubricants. These additives may be incorporated as required. The antibacterial polymer composition of the present invention may also contain liquids or organic solvents. When said composition is to be used as a shaped part, its shape and size are in no way limited. In order to provide the shaped part with an antimicrobial and/or microbicidal activity, it may be imparted to the whole part of the polymer, or if desired, to only part thereof. When the microbicidal polymer composition of the present invention is a shaped part, its microbicidal action is considered to be largely dependent on the silica gel-based antimicrobial composition present near the surface of the shaped part, so it may be advisable to provide the shaped part with a multilayer structure and treat its outer layer to acquire an antimicrobial and/or microbicidal activity. In the case of fibers, a core-/sheath yarn may be prepared by a known conjugate fiber spinning technique with the antimicrobial polymer composition of the present invention being used as the sheath component.

The following examples are provided for the purpose of further illustrating the present invention but are in no way to be taken as limiting.

First, the preparation of intermediate compositions from which to make the antimicrobial composition of the present invention is described below.

REFERENCE EXAMPLE 1

This reference example relates to the preparation of an intermediate composition that has a non-antimicrobial aluminosilicate layer on the surfaces of pores in a silica gel matrix and which is to be used as the precursor of the heat-resistant and weatherproof antimicrobial composition of the present invention.

Desalinated water (ca. 350 ml) was added to ca. 170 g of dried type B silica gel (20-40 mesh; >99.8% pure $SiO_2$) and the resulting mixture was agitated to form a homogeneous silica gel slurry. A dilute NAOH solution was added to the slurry and the pH of the mixture was held at 9.6. After adding ca. 330 ml of an aqueous solution containing 0.3 M $NaAlO_2$, the solution was agitated for ca. 10 h at a controlled temperature of 24°-25° C. After the end of the reaction, the product was filtered and the resulting solid phase was washed with water until the pH of the filtrate reached 9.7. The washed solid phase was then dried at 100°-110° C. to prepare an intermediate composition having a non-antimicrobial aluminosilicate layer on the surfaces of pores in the silica gel matrix.

REFERENCE EXAMPLE 2

This reference example also relates to the preparation of an intermediate composition that has a non-antimicrobial aluminosilicate layer on the surface of pores in a silica gel matrix and which is to be used as the precursor of the heat-resistant and weatherproof antimicrobial composition of the present invention. The conditions of preparation in this reference example were different from those adopted in Reference Example 1.

The silica gel material used in this reference example was the same as what was used in Reference Example 1. To 170 g of the dried product of that silica gel, ca. 330 ml of desalinated water was added and the resulting mixture was agitated to form a homogeneous silica gel slurry. A dilute NAOH solution was added to the slurry and the pH of the mixture was held at 9.49. Subsequently, ca. 400 ml of a solution of sodium aluminate (containing ca. 60 g of $NaAlO_2$) that was prepared by reaction between sodium hydroxide and aluminum hydroxide was added to the slurry containing solution and the resulting mixture was agitated at 24°–25° C. for ca. 8 h. After the solid-phase reaction product precipitated, filtration was conducted. The solid phase was then washed with water until its pH reached 9.8. The washed solid phase was dried at 100°–110° C. to prepare an intermediate composition having a non-antimicrobial aluminosilicate layer on the surfaces of pores in the silica gel matrix.

REFERENCE EXAMPLE 3

This reference example also relates to the preparation of an intermediate composition that has a non-antimicrobial aluminosilicate layer on the surface of pores in a silica gel matrix and which is to be used as the precursor of the heat-resistant and weatherproof antimicrobial composition of the present invention. The conditions of preparation in this reference example were different from those adopted in Reference Examples I and 2 and the reaction was carried out at an elevated temperature.

The silica gel material used in this reference example was the same as what was used in Reference Example 1. To 170 g of the dried product of that silica gel, ca. 350 ml of desalinated water was added and the resulting mixture was agitated to form a homogeneous silica gel slurry. A dilute NAOH solution was added to the slurry and the pH of the slurry-containing solution was held at 9.6. Subsequently, 400 ml of an aqueous solution of a sodium aluminate (containing 40 9 of $NaAlO_2$) was added to the slurry-containing solution, which was then agitated for 6 h at 60°±0.1° C. After the solid-phase reaction product precipitated, filtration was conducted and the resulting solid phase was washed with water until the pH of the filtrate reached near 9.8. Thereafter, the washed product was dried at 100°–110° C. to prepare an intermediate composition having a non-antimicrobial aluminosilicate layer on the surface of pores in the silica gel matrix.

A small portion was taken from each of the intermediate compositions having a non-antimicrobial layer on the surface of pores in the silica gel and heated under vacuum at near 350° C. to form an anhydride. The dried samples were precisely measured in amounts of 2–3 g and treated with a heated dilute nitric acid solution (2–2.5 N $HNO_3$) to have the sodium and aluminum in the solid phase eluted into the liquid phase. The two metals in the eluate were quantitatively determined by atomic-absorption spectroscopy and the results are shown in Table 1 below.

TABLE 1

| | Non-antimicrobial layer formed in silica gel matrix | | | |
|---|---|---|---|---|
| Ref. Ex. | Synthesis temperature, °C. | Metal content (anhydrous basis) Na % | Al % | Molar ratio Na/Al | Na, mmol/ (anhydrous basis) |
| 1 | 25 | 2.35 | 1.15 | 2.4 | 1.02 |
| 2 | 25 | 3.62 | 3.52 | 1.2 | 1.57 |
| 3 | 60 | 4.01 | 2.47 | 1.9 | 1.74 |

The contents of Na and Al in the anhydrous intermediate compositions prepared in Reference Examples 1–3, as well as their molar ratios are shown in Table 1. Both metals were present in the non-antimicrobial layer of each sample. Sodium (ion-exchangeable metal) was present in each sample in an amount not exceeding 6% and this is equivalent to the present of no more than 2.6 mmol of sodium per gram of said anhydrous composition As described above, in order to insure that the finally obtained antimicrobial composition has high heat and weather resisting properties, the contents of alkali metals in the non-antimicrobial layer of the intermediate composition must be held below the specified level. In all of the intermediate compositions prepared in Reference Examples 1–3, their alkali metal contents were within the preferred range.

Example 1

This example relates to the preparation of a silica gel based heat-resistant and weatherproof antimicrobial composition in which silver ions having microbicidal action are fixed in a stable manner to an aluminosilicate layer by ionic bonding.

In this example, the intermediate composition prepared in Reference Example 1 was used. An aqueous solution of silver nitrate (containing ca. 60 g of $AgNO_3$ in 1,000 ml of $H_2O$) was added to 100 g of the dried product of the intermediate composition. The resulting mixture was adjusted to a pH of 4.1, heated to 60° C. and stirred at that temperature for ca. 3 h. After the end of the ion-exchange reaction described hereinabove, filtration was conducted and the resulting solid phase was washed with water until all excess silver ions were removed from the solid phase. The washed solid phase was subsequently dried at 100°–110° C. to prepare a silica gel based heat-resistant and weatherproof antimicrobial composition.

This antimicrobial composition had SSA and PV of 322 $m^2/g$ and 0.68 $cm^3/g$, respectively, both being on an anhydrous basis. The amounts of silver and sodium in this composition were 5.20% and 1.23% respectively. The amounts of silver and sodium corresponded to 0.47 and 0.53 equivalent fractions, respectively. The silver content was equivalent to 0.15 mmol Ag per 100 $m^2$ of the anhydrous antimicrobial composition. This can be easily calculated from the silver content of the antimicrobial composition and its SSA. Needless to say, silver was fixed in a stable manner to the antimicrobial layer by ionic bonding. The thus prepared composition is hereunder designated sample S-2. Using the intermediate composition made in Reference Example 1, samples S-1, S-3 and S-5 were prepared in the same manner except that the concentration of the silver nitrate solution was varied. Sample S-4 containing both silver and zinc as antimicrobial metals was prepared using the intermediate composition made in Reference Example 1; to prepare that sample, the intermediate composition was subjected to ion-exchange with a liquid mixture of silver nitrate and zinc nitrate, whereby silver and zinc were fixed to the non-antimicrobial layer.

EXAMPLES 2 and 3

These examples relate to the preparation of silica gel based heat-resistant and weatherproof antimicrobial compositions in which either copper or zinc ion is fixed in a stable manner to an aluminosilicate layer by ionic bonding.

In these examples, the intermediate composition prepared in Reference Example I was used. To ca. 30 g of the dried product of that intermediate composition, 160 ml of 0.4 M $CuSO_4$ solution (Example 2) or 150 ml of 0.38 M $ZnSO_4$ solution (Example 3) was added. Each of the resulting mixtures was adjusted to a pH of 3.9 and stirred for ca. 4 h at a controlled temperature of 25° C. to carry out an ion-exchange reaction. Subsequently, filtration was conducted and the resulting solid phase was washed with water until copper ions (Example 2) or zinc ions (Example 3) were no longer present in the solid phase. After the end of the washing, the solid phase was dried at 100°–110° C. to prepare two samples of the silica gel based heat-resistant and weatherproof antimicrobial composition of the present invention which had an antimicrobial layer formed on the surface of pores in the silica gel matrix with copper ions (Example 2) or zinc ions (Example 3) retained as antimicrobial metal ions.

In preparing the antimicrobial composition of the present invention, the intermediate composition as prepared in Reference Example 1 that had a non-antimicrobial layer on the surface of pores in the silica gel matrix was used. in Examples 1–3. The intermediate composition contained 2.35% of ion-exchangeable sodium which was present on the non-antimicrobial layer. When such low content of sodium was ion-exchanged using solutions containing antimicrobial metals, the finally obtained antimicrobial compositions would naturally contain sodium in amounts smaller than 2.35%. For instance, the heat-resistant and weatherproof antimicrobial composition prepared in Example 1 contained 1.23% sodium (on an anhydrous basis), which was obviously present in the antimicrobial layer. This low content of sodium contributed to improvements in the heat resistance and weatherproofness of the antimicrobial compositions. The antimicrobial composition having this low sodium content have the added advantage that they can be incorporated in various polymers to yield antimicrobial polymers having markedly improved weatherproofness. The samples prepared in Examples 2 and 3 shall hereunder be designated S-7 and S-6, respectively.

The amounts of copper and sodium in the antimicrobial composition S-7 were 2.04% and 0.90%, respectively, on an anhydrous basis. The copper content was equivalent to 0.10 mmol Cu per 100 $m^2$ of the anhydrous antimicrobial composition. The amounts of zinc and sodium in the antimicrobial composition S-6 were 1.27% and 1.45%, respectively, on an anhydrous basis. The zinc content was equivalent to 0.06 mmol Zn per 100 $m^2$ of the anhydrous antimicrobial composition. Needless to say, the antimicrobial metals (i.e., Cu and Zn) were fixed in a stable manner to the antimicrobial layer by ionic bonding.

The Cu containing antimicrobial composition prepared in Example 2 or the Zn containing antimicrobial composition prepared in Example 3 is typically used in combination with the Ag-containing antimicrobial composition which is also prepared in accordance with the present invention. Antimicrobial compositions containing two different antimicrobial metals (e.g. Ag combined with Cu, or Ag combined with Zn) may be prepared by subjecting the intermediate composition having a non-antimicrobial layer to ion-exchange with a solution containing both silver and some other suitable antimicrobial metal in accordance with the method already described hereinabove.

EXAMPLE 4

Water (ca. 100 ml) was added to ca. 30 g of the dried product of the intermediate composition (20–40 mesh) prepared in Reference Example 3. The resulting mixture was adjusted to a pH of ca. 4 under agitation. To the so adjusted mixture, a solution of silver nitrate (containing 3 g of $AgNO_3$ in 80 ml of $H_2O$) was added and an ion-exchange reaction was carried at room temperature for ca. 4 h under stirring. The thus obtained silver-containing antimicrobial composition was filtered, washed and dried in the usual manner. The resulting sample is hereunder designated S-8. The characteristics of samples S-1 to S-8 are shown in Table 2 below.

TABLE 2

| Sample | SSA $m^2/g$ | PB $cm^3/g$ | Na content wt % | Na content mmol/g | Antimicrobial metal Species | Amount wt % | Amount mmol/g | Amount mmol/100 $m^2$ |
|---|---|---|---|---|---|---|---|---|
| S-1 | 317 | — | 0.68 | 0.30 | Ag | 7.81 | 0.72 | 0.23 |
| S-2 | 322 | 0.68 | 1.23 | 0.53 | Ag | 5.20 | 0.48 | 0.15 |
| S-3 | 366 | — | 2.00 | 0.87 | Ag | 1.56 | 0.14 | 0.039 |
| S-4 | 314 | — | 0.77 | 0.33 | Ag Zn | 2.96 1.35 | 0.48 (total) | 0.153 (total) |
| S-5 | 359 | — | 1.93 | 0.84 | Ag | 1.94 | 0.18 | 0.50 |
| S-6 | 328 | 0.67 | 1.45 | 0.63 | Zn | 1.27 | 0.19 | 0.06 |
| S-7 | 319 | 0.69 | 0.90 | 0.39 | Cu | 2.04 | 0.32 | 0.10 |
| S-8 | 373 | 0.73 | 3.75 | 1.63 | Ag | 1.11 | 0.10 | 0.028 |

The antimicrobial activity of the samples was evaluated.

Methods of Evaluating Antimicrobial Activity

The following three methods were employed to evaluate the antimicrobial activity of the antimicrobial compositions: (1) growth inhibition zone formation test; (2) measurement of minimum growth inhibitory concentration (MIC); and (3) counting the number of viable cells over time by the "shake flask (SF) method" specified by the Fibrous Product Sanitary Processing Conference.

In evaluating the antimicrobial activity of each sample, the following microorganisms were used:

| | |
|---|---|
| *Escherichia coli* | IFO-12734 |
| *Stahylococcus aureus* | IFO-12732 |
| *Pseudomonas aeruginosa* | IFO-12689 |
| *Asperillus niger* | IFO-31125 |
| *Bacillus subtilis* | IFO-13719 |

The following media were used:
Mueller Hinton 2 (BBL) for bacterial growth;
Sabouraud Dextrose Agar (BBL) for fungal growth (1) Inhibition Zone Formation Test The test sample was suspended at a concentration of 100 mg/ml and impregnated in a disk (13 mm$\phi$). The test microorganism was suspended in a phosphate buffer solution 1/15 M; pH=7.2) at a concentration of $10^8$ cells/ml and 0.1 ml of the suspension was dispersed in the media with a Conradi's rod. The disk impregnated with the test sample was plated on the media and checked for the formation of an inhibition zone. The microorganisms and media used in this test were as specified above.

(2) Measurement of minimum growth inhibitory concentration (MIC)

(i) Preparation of a cell suspension of bacterium

The cells of a test bacterium that had been cultivated in a common agar medium at 37° C. for 18 hours were suspended in a phosphate buffer (1/15 M; pH 7.2) at a concentration of $10^8$ cells/ml and diluted as appropriate for the test.

(ii) Preparation of a cell suspension of fungus

Conidia of a test fungus that had been cultivated on a slant potato dextrose agar medium at 25° C. for 7 days were suspended in physiological saline containing sterile 0.05% polysorbate to prepare a suspension at a concentration of $10^7$ cells/ml, which was diluted as appropriate for the test.

(iii) MIC measurement

A test sample was suspended in a phosphate buffer solution at a concentration of $2 \times 10^4$ ppm and serially diluted two-fold to construct 10 levels of density gradient. A 1-ml portion of each density was poured into a Petri dish and mixed with an agar medium (9 ml) to solidify. Each of the test microorganisms was streak cultured for 48 h and evaluated for MIC. The microorganisms and media used in the MIC measurement were as specified above.

(3) Counting of cells over time

The counting of cells was conducted at given time intervals by the shake flask (SF) method.

(i) Preparation of a cell suspension of bacterium

Same as described under 2(ii) of "MIC measurement".

(ii) Preparation of a cell suspension of fungus

Same as described under 2(i) of "MIC measurement".

(iii) Test by the SF method

A phosphate buffer solution (50 ml or 100 ml) containing a predetermined amount of a test sample was put into a 200-ml conical flask, which was subsequently charged with a suspension of test microorganism at a concentration of $10^5$ or $10^6$ cells/ml and shaken at 25° C. for a predetermined time while the number of viable cells was counted at given time intervals. The microorganisms and media used in the test by the SF method were as specified above.

Inhibition Zone Formation Test.

Samples S-1 to S-4 were effective against four common bacteria, *Escherichia coli*, *Staphylococcus aureus*, *Pseudomarias aeruginosa*, *Aspergillus niger* and *Bacillus subtilis*, forming an inhibition zone in all of these four cases. Samples S-1 to S-4 were also effective against a fungus *Aspergillus niger*, forming an inhibition zone (see Table 3). P-1 (see Reference Example 1: the fine powder of an intermediate composition having a non-antimicrobial layer on the surfaces of pores in a silica gel matrix) and P-2 (the fine powder of starting silica gel material used in Reference Examples 1-3) that are shown in Table 3 were specimens for a blank test and they were incapable of forming an inhibition zone against bacteria or fungi.

TABLE 3

| | Inhibition Zone Formation Test Test Microorganism | | | | |
|---|---|---|---|---|---|
| Sample | Escherichia coli | Pseudomonas aeruginosa | Staphylococcus aureus | Bacillus Subtilis | Aspergillus niger |
| S-1 | + | + | + | + | + |
| S-2 | + | + | + | + | + |
| S-3 | + | + | + | + | + |
| S-4 | + | + | + | + | + |
| P-1 | − | − | − | − | − |
| P-2 | − | − | − | − | − |

S-1 to S-4: The fine powders of antimicrobial compositions within the scope of the present invention
P-1: The fine powder of an intermediate composition having a non-antimicrobial layer on the surfaces of pores in a silica gel matrix (Reference Example 1)
P-2: The fine powder of starting silica gel material (as used in Reference Examples 1-3)

MIC measurement

The minimum growth inhibitory concentrations (MIC) of representative examples of the silica gel based heatresistant and weatherproof antimicrobial composition of the present invention were measured by the aforementioned method and the results were as shown in Table 5.

Sample S-1 contained more silver than sample S-2 in the anhydrous antimicrobial composition but both had the same MIC value of 7.8 ppm against *Escherichia coli* and *Pseudomonas aeruginosa*, and 15.6 ppm against *Staphylococcus aureus* and *Aspergillus niger*.

Sample S-1 had an MIC value of 7.8 ppm against *Bacillus subtilis* and S-2 had a value of 15.6 ppm. With the error of MIC measurement taken into account, the two samples may as well be considered to have comparable MIC values against bacteria and fungi. Sample S-5 contained less silver than S-1 and S-2 and, hence, as shown in Table 5, S-5 showed larger MIC values against bacteria and fungi than S-1 and S-2. For comparison with the antimicrobial compositions of the present invention, the MIC values of three known types of antimicrobial zeolites (O-1, O-2 and O-3) are shown in Table 5. The characteristics of O-1 to O-3, as well as comparative samples O-4 and O-5 which will be discussed later, are shown in Table 4.

TABLE 4

| Sample | Particle size $D_{av}$ μm | Specific surface area m²/g | Na content wt % | Na content mmol/g | Antimicrobial metal Species | Antimicrobial metal wt % | Antimicrobial metal mmol/g |
|---|---|---|---|---|---|---|---|
| O-1 | 3 | 584 | 7.8 | 3.39 | Ag | 3.36 | 1.28 |
| | | | | | Cu | 6.18 | |
| O-2 | 2.6 | 597 | 6.5 | 2.83 | Ag | 2.59 | 2.15 |
| | | | | | Zn | 12.48 | |
| O-3 | 3.1 | 613 | 15.1 | 6.57 | Ag | 3.3 | 0.31 |
| O-4 | 3.4 | — | ca.14 | ca.6 | Ag | 5.31 | 0.49 |
| O-5 | 3.8 | — | ca.14 | ca.6 | Cu | 2.18 | 0.34 |

TABLE 5

Minimum Growth Inhibitory Concentration (MIC)

| Sample | Escherichia coli | Pseudomonas aeruginosa | Staphylococcus aureus | Bacillus Subtilis | Aspergillus niger |
|---|---|---|---|---|---|
| S-1 | 7.8 | 7.8 | 15.6 | 7.8 | 15.6 |
| S-2 | 7.8 | 7.8 | 15.6 | 15.6 | 15.6 |
| S-5 | 62.5 | 62.5 | 125 | 62.5 | 125 |
| S-8 | 250 | — | — | 500 | — |
| O-1 | 125 | 62.5 | 125 | 62.5 | 250 |
| O-2 | 250 | 250 | 250 | 250 | 250 |
| O-3 | 125 | 125 | 250 | — | 250 |

S-1, S-2, S-5 and S-8: Antimicrobial composition of the present invention
O-1, O-2 and O-3: Antimicrobial zeolite As shown in Table 5, the MIC value against bacteria and fungi can be lowered by using S-1, S-2 and S-5 (the heat-resistant and weatherproof antimicrobial compositions of the present invention having an antimicrobial layer on the surfaces of pores in a silica gel matrix) as compared with O-1, O-2 and O-3 (the known antimicrobial zeolite). In other words, S-1, S-2 and S-5 were better antimicrobial agents than O-1, O-2 and O-3. Known antimicrobial zeolite 0-3 contained 3.3% Ag whereas S-5, an antimicrobial composition of the present invention, contained 1.94% Ag. S-5 had lower MICs against $Escherichia\ coli$, $Pseudomonas\ aeruginosa$ and $Staphylococcus\ aureus$ than O-3. A similar tendency was observed with a fungus ($Aspergillus\ niger$) in that S-5 had a smaller MIC than O-3. The silver content of O-3 was higher than that of S-5 but, unexpectedly enough, O-3 had higher MICs against bacteria and fungi than S-5. As is evident from the results of MIC measurements, the antimicrobial compositions of the present invention exhibited by far stronger antimicrobial action than the known antimicrobial zeolites and this difference in antimicrobial effect would have resulted from the essential structural difference between the two types of antimicrobial agents.

Counting cells over time

Using the two types of antimicrobial agents, the death rates of bacteria and fungi (changes in cell counts with time) were measured under various conditions. As a result, it was for the first time discovered by the present inventors that the antimicrobial compositions of the present invention were capable of killing microorganisms at faster speed than the known antimicrobial zeolites. Details are given below with reference to the test results.

TABLE 6

Evaluation of Antimicrobial Activity of SF Method
(test microorganism, $Aspergillus\ niger$; initial cell count,
$1.7 \times 10^6$ cells/ml; temperature, 25° C.; total suspension volume, 50 ml;
test sample, antimicrobial compositions of the present invention
and known antimicrobial zeolites)

| Run No. | Sample Designation | Sample Amount | Antimicrobial metal and its content | Time-dependent change in cell count (No. of viable cells per ml) 5 | 10 | 20 | 60 | 180 (min) |
|---|---|---|---|---|---|---|---|---|
| 1 | S-3 | 100 mg/50 ml | Ag = 1.6 mg | 0 | 0 | 0 | — | — |
| 2 | S-3 | 250 mg/50 ml | Ag = 4 mg | 0 | 0 | 0 | — | — |
| 3 | O-1 | 50 mg/50 ml | Ag = 1.7 mg Cu = 3.1 mg | — | — | $5.7 \times 10^5$ | $8.1 \times 10^4$ | $3.9 \times 10^3$ |
| 4 | O-1 | 125 mg/50 ml | Ag = 4.3 mg Cu = 7.8 mg | — | — | $4.3 \times 10^5$ | $5.8 \times 10^4$ | $7.4 \times 10^2$ |
| 5 | O-1 | 200 mg/50 ml | Ag = 6.8 mg Cu = 12.4 mg | — | — | $2.1 \times 10^5$ | $3.6 \times 10^4$ | $8.9 \times 10$ |
| 6 control | — | — | — | $1.1 \times 10^6$ | $9.8 \times 10^5$ | $8.3 \times 10^5$ | $7.1 \times 10^5$ | $6.0 \times 10^5$ |

In order to compare the antimicrobial activity of an antimicrobial composition of the present invention with that of a known antimicrobial zeolite, the time-dependent changes in the cell count of $Aspergillus\ niger$ were measured by the SF method under the test conditions shown in Table 6. Run 6 was a blank test conducted for comparison in the absence of any antimicrobial agent. In Runs 1 and 2, the fine powder of S-3 (an antimicrobial composition within the scope of the present invention) was used in the amounts shown in Table 6. In both runs, the fungus $Aspergillus\ niger$ was completely killed in 5 minutes. In Runs 3, 4 and 5, the time-dependent changes in the cell count of $Aspergillus\ niger$ were measured for varying amounts of a known antimicrobial zeolite, O-1. In Run 3, 0-1 was used in an amount of 50 mg per 50 ml (Ag=1.7 mg; Cu=3.1 mg) and the number of viable cells of $Aspergillus\ niger$ was $5.7 \times 10^5$ cells/ml after the passage of 20 min, $8.1 \times 10^4$ cells/ml, after the passage of 1 h, and $3.9 \times 10^3$ cells/ml (equivalent to a death rate of 99.8%) after the passage of 3 h.

In Run 4, O-1 was used in a larger amount (125 mg/50 ml; Ag=4.3 mg; Cu=7.8 mg) than in Run 3. As in Run 3, not all the $Aspergillus\ niger$ cells could be killed even after the passage of 3 h and $7.4 \times 10^2$ cells remained alive per ml, which was equivalent to a death rate of 99.96%. In Run 5, O-1 was used in a larger amount (200 mg/50 ml Ag=6.8 mg; Cu=12.4 mg; $D_{av}$=3 pm) than in Run 4 and yet the number of viable $Aspergillus\ niger$ cells was $2.1 \times 10^5$ per ml (death rate, 87.65%) after the passage of 20 min. Even after the passage of 3 h, not all cells could be killed and $8.9 \times 10$ cells remained alive per ml, which was equivalent to a death rate of 99.99%. In Run 1 using S-3, the content of an antimicrobial metal (Ag) was 1.6 mg. In Run 3, the antimicrobial zeolite (O-1-) contained 1.7 mg of Ag and 3.1 mg of Cu as antimicrobial metals. Comparing the results of the two runs, one can readily see that S-3, or the antimicrobial composition of the present invention, was capable of killing the fungus at a remarkably faster speed than O-1, the known antimicrobial zeolite. In Run 2, S-3 was used in an amount of 250 mg/50 ml (Ag=4 mg) and the death rate of $Aspergillus\ niger$ was 100% in 5 min. In Run 4 where O-1 was used in an amount of 125 mg/50 ml (Ag=4.3 mg; Cu=7.8 mg), not all of the $Aspergillus\ niger$ cells could be killed after the passage of 3 h and $7.4 \times 10^2$ cells remained alive per ml. The contents of antimicrobial metals were greater in Run 4 than in Run 2 and yet by far better results of antifungal action were attained in Run 2. Hence, it was for the first time discovered by the present inventors that S-3, or an antimicrobial composition of the present invention, was capable of killing *Aspergillus niger* at a surprisingly higher speed than O-1, a known antimicrobial zeolite.

In the next place, the antimicrobial activity of the heat-resistant and weatherproof composition of the present invention that contained zinc as an antimicrobial metal on the surfaces of pores in a silica gel matrix was evaluated by the SF method and the results are An antimicrobial test was conducted by the SF method using a known antimicrobial zeolite, O-3, under the conditions shown in Table 9-A in order to evaluate its efficacy against *Staphylococcus aureus*. In Run 20, the time-dependent change in cell count was measured using the powder of O-3. The number of viable cells was $2 \times 10^3$ per ml (99.9% as death rate) after the passage of 30 min and the death rate of the microorganism was 100% after the passage of 2 h. In Run 21, the same measurement was conducted using O-3 in an amount of 6 mg/100 ml (Ag=0.20 mg).

TABLE 9-A

Evaluation of Antimicrobial Activity by SF Method (test microorganism, *Staphylococcus aureus*; initial cell count, $2.3 \times 10^6$ cells/ml; temperature, 25° C.; total suspension volume, 100 ml; test sample, antimicrobial zeolite, O-3)

| Run No. | Sample Designation | Sample Amount | Content of antimicrobial metal (Ag) | Time-dependent change in cell count (No. of viable cells per ml) 0 | 0.5 | 2 (h) |
|---|---|---|---|---|---|---|
| 20 | O-3 | 21 mg/100 ml | 0.69 mg | $2.3 \times 10^6$ | $1.2 \times 10^3$ | 0 |
| 21 | O-3 | 6 mg/100 ml | 0.20 mg | $2.3 \times 10^6$ | $6.1 \times 10^4$ | 0 |
| 22 | control | — | — | $2.3 \times 10^6$ | $2.3 \times 10^6$ | $2.2 \times 10^6$ | shown in Table 7. In the evaluation, S-6 was used as a sample and its ability to kill *Bacillus subtilis* was as shown in Table 7. When S-6 was used in an amount of 50 mg/50 ml (Zn=0.64 mg), the death rate of *Bacillus subtilis* was 96.6% after the passage of 8 h; when S-6 was used in an amount of 250 mg/50 ml (Zn=3.2 mg), the death rate of *Bacillus subtilis* was 96.9% after the passage of 8h. Run 1.2 was a blank test conducted for comparison in the absence of any antimicrobial agent.

After the passage of 30 min, the number of viable *Staphylococcus aureus* cells was $6.1 \times 10^4$ per ml (equivalent to a death rate of 97.4%). All the cells were found dead after the passage of 2 h. Run 22 was a blank test conducted as a control in the absence of any antimicrobial agent.

A similar test was conducted using antimicrobial compositions of the present invention (S-1, S-2 and S-5). The results are shown in Table 9-B. Run 26 was a blank

TABLE 7

Evaluation of Antimicrobial Activity by SF Method (test microorganism, *Bacillus subtilis*; initial cell count, $7.3 \times 10^6$ cells/ml; temperature, 25° C.; total suspension volume, 50 ml; test sample, antimicrobial composition, S-6, of the present invention)

| Run No. | Sample Designation | Sample Amount | Antimicrobial metal and its content | Time-dependent change in cell count (No. of viable cells per ml) 0.5 | 8 (h) |
|---|---|---|---|---|---|
| 10 | S-6 | 50 mg/50 ml | Zn = 0.64 mg | $6.7 \times 10^6$ | $2.5 \times 10^5$ |
| 11 | S-6 | 250 mg/50 ml | Zn = 3.2 mg | $5.8 \times 10^6$ | $2.3 \times 10^5$ |
| 12 | control | — | — | $6.9 \times 10^6$ | $3.1 \times 10^6$ |

The same test was conducted using sample S-7 and its ability to kill *Bacillus subtilis* was as shown in Table 8. In the SF test using *Bacillus subtilis* at an initial concentration of $7.7 \times 10^6$ cells/ml, S-7 was employed in an amount of 50 mg/50 ml (Cu=1.0 mg) and the count of viable cells was $3.9 \times 10^6$ and $5.1 \times 10^2$ cells per ml after the passage of 0.5 and 2 h, respectively. The former value was equivalent to a death rate of 49.4% and the latter value was equivalent to a death rate of 99.99%. After the passage of 4 h, it was found that all *Bacillus subtilis* had been killed. In Run 14 where S-7 was used in a larger amount (250 mg/50 ml; Cu=5.0 mg) than in Run 13, the number of viable *Bacillus subtilis* cells was $1.6 \times 10^6$ per ml (equivalent to a death rate of 79.22%) after the passage of 0.5 h and all cells were found to have been killed after the passage of 2 h. Run 15 was a blank test conducted for comparison in the absence of any antimicrobial agent.

test conducted as a control in the absence of any antimicrobial agent. In Run 25, the efficacy of S-5 (10 mg/100 ml; Ag=0.19 mg) against *Staphylococcus aureus* was evaluated by the SF method. After the passage of 5 and 10 min, the number of viable *S. aureus* cells was $4.3 \times 10^3$ (99.7% death rate) and $7.2 \times 10$ (99.99% death rate), respectively, per ml. After the passage of 15 min, all cells were found to be dead. In Run 24, S-2 (5 mg/100 ml; Ag =0.26 mg) was used. After the passage of 5 and 10 min, the number of viable *S. aureus* cells was $1.8 \times 10^3$ (99.9% death rate) and $1.1 \times 10$ (99.99% death rate), respectively, per ml. After the passage of 15 min, all cells were found to be dead.

In Run 23, the efficacy of the fine powder of S-1 (8 mg/100 ml; Ag=0.62 mg), an antimicrobial composition containing the antimicrobial metal Ag in a large amount than S-2 and S-5 used in Runs 24 and 25, was evaluated by the SF method. As Table 9-B shows, all S. aureus were found to be dead in only 5 min.

TABLE 8

Evaluation of Antimicrobial Activity by SF Method (test microorganism, *Bacillus subtilis*; initial cell count. $7.7 \times 10^6$ cells/ml; temperature, 25° C.; total suspension volume, 50 ml; test sample, antimicrobial composition, S-7, of the present invention)

| Run No. | Sample Designation | Sample Amount | Antimicrobial metal and its content | Time-dependent change in cell count (No. of viable cells per ml) 0.5 | 1 | 2 | 4 (h) |
|---|---|---|---|---|---|---|---|
| 13 | S-7 | 50 mg/50 ml | Cu = 1.0 mg | $3.9 \times 10^6$ | $5.6 \times 10^4$ | $5.1 \times 10^2$ | 0 |
| 14 | S-7 | 250 mg/50 ml | Cu = 5.0 mg | $1.6 \times 10^6$ | $8.9 \times 10$ | 0 | 0 |
| 15 | control | — | — | $7.8 \times 10^6$ | $7.6 \times 10^6$ | $6.8 \times 10^6$ | $5.9 \times 10^6$ |

TABLE 9-B

Evaluation of Antimicrobial Activity by SF Method
(test microorganism, *Staphylococcus aureus*; initial cell count, 1.3 × 10⁶ cells/ml;
temperature, 25° C.; total suspension volume, 100 ml; test sample, S-1, S-2 and S-5)

| Run No. | Sample Designation | Amount | Content of antimicrobial metal (Ag) | Time-dependent change in cell count (No. of viable cells per ml) 0 | 5 | 10 | 15 (min) |
|---|---|---|---|---|---|---|---|
| 23 | S-1 | 8 mg/100 ml | 0.62 mg | $1.3 \times 10^6$ | 0 | 0 | 0 |
| 24 | S-2 | 5 mg/100 ml | 0.26 mg | $1.3 \times 10^6$ | $1.8 \times 10^3$ | $1.1 \times 10$ | 0 |
| 25 | S-5 | 10 mg/100 ml | 0.19 mg | $1.3 \times 10^6$ | $4.3 \times 10^3$ | $7.2 \times 10$ | 0 |
| 26 | control | — | | $1.3 \times 10^6$ | $1.1 \times 10^6$ | $1.2 \times 10^6$ | $1.2 \times 10^6$ |

Comparing the data in Table 9-A with that in Table 9-B, one can readily see that the antimicrobial compositions of the present invention which had an antimicrobial metal containing layer on the surfaces of pores in a silica gel matrix had an outstandingly higher antimicrobial action than the known antimicrobial zeolites and that they were capable of killing *S. aureus* at a very fast rate. It is also obvious that the antimicrobial compositions of the present invention were much more effective against *S. aureus* than the known antimicrobial zeolite even when the antimicrobial metal (Ag) content was adjusted to be the same. This drastic difference in antimicrobial activity would be due to the essential structural difference between the two types of antimicrobial agents.

An antimicrobial activity test was also conducted by performing the SF method with *Escherichia coli* used as a common bacterium and the results are shown in Table 10. In the test, S-1 and S-5 were used as samples of the antimicrobial composition of the present invention. The powder of O-3, the already discussed known antimicrobial zeolite, was used as a comparison. In Run 31, S-5 was used (10 mg/100 ml; Ag=0.19 mg). After the passage of 10 min, the number of viable *E. coli* cells was 4.2×10³ per ml (equivalent to a death rate of 99.8%) and after the passage of 30 min, all cells were found to be dead. In Run 30, S-1 (8 mg/100 ml; Ag=0.62 mg) was used and it contained more antimicrobial metal (Ag) than in Run 31. In this case, all *E. coli* cells were found dead after the passage of 10 min. In Runs 32 and 33, O-3 was used in respective amounts of 21 mg/100 ml (Ag=0.69 mg) and 6 mg/100 ml (Ag=0.20 mg). After the passage of 10 min, the viable cell count was 2.9×10⁵ cells/ml (87.4% death rate) in Run 32 and 5.7×10⁵ cells/ml (75.2% death rate) in Run 33. After the passage of 30 min, all *E. coli* cells were found dead in both Runs 32 and 33. Run 34 was a blank test conducted as a control in the absence of any antimicrobial agent.

TABLE 10

Evaluation of Antimicrobial Activity by SF Method (test microorganism, *Escherichia coli*;
initial cell count, 2.3 × 10⁶ cells/ml; temperature, 25° C.; total suspension volume, 100 ml;
test sample, antimicrobial zeolite, O-3 and S-1 and S-5 of the present invention)

| Run No. | Sample Designation | Amount | Content of antimicrobial metal (Ag) | Time-dependent change in cell count (No. of viable cells per ml) 0 | 10 | 30 (min) |
|---|---|---|---|---|---|---|
| 30 | S-1 | 8 mg/100 ml | 0.62 mg | $2.3 \times 10^6$ | 0 | 0 |
| 31 | S-5 | 10 mg/100 ml | 0.19 mg | $2.3 \times 10^6$ | $4.2 \times 10^3$ | 0 |
| 32 | O-3 | 21 mg/100 ml | 0.69 mg | $2.3 \times 10^6$ | $2.9 \times 10^5$ | 0 |
| 33 | O-3 | 6 mg/100 ml | 0.20 mg | $2.3 \times 10^6$ | $5.7 \times 10^5$ | 0 |
| 34 | control | — | | $2.3 \times 10^6$ | $2.4 \times 10^6$ | $1.9 \times 10^6$ |

Comparing Runs 30 and 32 in which the antimicrobial metal content was substantially the same, one can readily see that the antimicrobial composition of the present invention was more effective against *E. coli* than the known antimicrobial zeolite.

An antifungal efficacy test was conducted by the SF method and the results are shown in Tables 11 and 12. In the test described in Tables 11 and 12, the initial cell count of *Aspergillus niger* (6.1×10⁵ cells/ml) and the sample species were different than in the test described in Table 6. An antifungal activity test was also conducted as a comparison using a known antimicrobial zeolite (see Table 12). In Run 41, sample S-1 was used and, in Runs 42, 43 and 44, the fine powder of sample S-2 was used.

TABLE 11

Evaluation of Antifungal Activity by SF Method
(test microorganism, *Aspergillus niger*; initial cell count, 6.1 × 10⁵ cells/ml; temperature,
25° C.; total suspension volume, 50 ml; test sample, S-1 and S-2 of the present invention)

| Run No. | Sample Designation | Amount | Content of antimicrobial metal (Ag) | Time-dependent change in cell count (No. of viable cells per ml) 0 | 5 | 10 | 20 (min) |
|---|---|---|---|---|---|---|---|
| 40 | control | — | | $6.1 \times 10^5$ | $6.2 \times 10^5$ | $5.9 \times 10^5$ | $4.7 \times 10^5$ |
| 41 | S-1 | 68 mg/50 ml | 5.3 mg | $6.1 \times 10^5$ | 0 | 0 | 0 |
| 42 | S-2 | 25 mg/50 ml | 1.3 mg | $6.1 \times 10^5$ | $2.0 \times 10^4$ | $1.4 \times 10^3$ | 0 |
| 43 | S-2 | 13 mg/50 ml | 0.7 mg | $6.1 \times 10^5$ | $4.7 \times 10^4$ | $1.6 \times 10^3$ | 0 |
| 44 | S-2 | 40 mg/50 ml | 2.1 mg | $6.1 \times 10^5$ | $1.4 \times 10^3$ | $2.1 \times 10$ | 0 |

TABLE 12

Evaluation of Antimicrobial Activity by SF Method
(test microorganism, *Aspergillus niger*; initial cell count, 6.1 × 10$^5$ cells/ml; temperature, 25° C.; total suspension volume, 50 ml; test sample, O-3 of known antimicrobial zeolite)

| Run No. | Sample Designation | Sample Amount | Content of antimicrobial metal (Ag) | Time-dependent change in cell count (No. of viable cells per ml) 0 | 5 | 10 | 15 (min) |
|---|---|---|---|---|---|---|---|
| 45 | O-3 | 160 mg/50 ml | 5.3 mg | 6.1 × 10$^5$ | 2.9 × 10$^5$ | 2.2 × 10$^3$ | 6.1 × 10 |
| 46 | O-3 | 64 mg/50 ml | 2.1 mg | 6.1 × 10$^5$ | 3.8 × 10$^5$ | 3.6 × 10$^3$ | 1.2 × 10$^2$ |
| 47 | O-3 | 23 mg/50 ml | 0.8 mg | 6.1 × 10$^5$ | 4.1 × 10$^5$ | 5.3 × 10$^3$ | 7.6 × 10$^2$ |
| 48 | control | — | — | 6.1 × 10$^5$ | 6.0 × 10$^5$ | 6.1 × 10$^5$ | 9.4 × 10$^4$ |

In Run 41 (Table 11), S-1 was used in an amount of 68 mg/50 ml (Ag=5.3 mg) and all *A. niger* cells were already found dead after the passage of 5 min. In Run 43, S-2 was used in an amount of 13 mg/50 ml (Ag=0.7 mg) and, after the passage of 5 and 10 min, the viable cell count was 4.7×10$^4$ (92.3% death rate) and 1.6×10$^3$ (99.97% death rate), respectively, per ml After the passage of 20 min, all A. niger cells were found dead. In Run 42, S-2 was used in an amount of 25 mg/50 m9- (Ag =1.3 mg) and, after the passage of 5 and 10 min, the viable cell count was 2.0×10$^4$ (99.67% death rate) and 1.4×10$^3$ (99.98% death rate), respectively, per ml After the passage of 20 min, all *A. niger* cells were found dead. In Run 44, S-2 (40 mg/50 ml; Ag=2.1 mg) was used and it contained more antimicrobial metal Ag in a larger amount than in Runs 42 and 43. The viable cell count was 1.4×10$^3$ cells/ml (99.98% death rate) and 2.1×10 cells/ml (99.99% death rate) after the passage of 5 and 10 min, respectively. After 20 min, all *A. niger* cells were found to be dead.

The antifungal activity test the results of which are shown in Table 12 was conducted using the known antimicrobial zeolite O-3. In Run 47, 0-3 was used in an amount of 23 mg/50 ml (Ag=0.8 mg). The number of viable *Aspergillus niger* cells was 4.1×10$^5$ (32.8% death rate) and 5.3×10$^3$ (99.1%) per ml after the passage of 1 and 3 h, respectively. Even after the passage of 5 h, the viable cell count was 7.6×10$^2$ cells/ml (equivalent to a death rate of 99.98%). Tn Runs 45 and 46, 0-3 was used in larger amounts than in Run 47; in Run 45, 0-3 was used in an amount of 1-60 mg/50 ml (Ag=5.3 mg) and in Run 46, 0-3 was used in an amount of 64 mg/50 ml (Ag=2.1 mg). The viable cell count after 5 h was 6.2×10 cells/ml (99.99% death rate) in Run 45 and 1.2×10$^2$ cells/ml (99.98% death rate) in Run 46. In each run, not all *A. niger* cells were found dead even after the passage of 5 h. On the other hand, S-1 and S-2 of the present invention were capable of totally annihilating the fungus within 20 min. The data in Tables 11 and 12 show that the antimicrobial compositions of the present invention are by far superior to the known antimicrobial zeolite in antifungal efficacy and that the fungicidal speed of the former was incomparably faster than that of the latter. This significant difference in antifungal action is one of the characteristic features of the present invention and would be ascribable to the already discussed essential structural difference between the two types of antimicrobial agents.

EXAMPLE 5

This example describes the results of a heat resistance test conducted on the antimicrobial composition of the present invention. In the test, samples S-2, S-4, S-7 and S-8 were used, with known antimicrobial zeolite O-3 being used as a comparison. The test results are shown in Table 13 below.

TABLE 13

Heat Resistance Test on the Antimicrobial Composition of the Invention

| Run No. | Sample | 200° C. × 3 h | 300° C. 3 h | 450° C. × 3 h |
|---|---|---|---|---|
| 1 | S-2 Ag = 5.20% | white | white | white |
| 2 | S-4 Ag = 2.96% Zn = 1.35% | white | white | white |
| 3 | S-7 Cu = 2.04% | blue | blue | blue |
| 4 | S-8 Ag = 1.11% | white | white | white |
| 5 | antimicrobial zeolite O-3 (NaAgZ; Ag = 3.3%) | white | grayish white | grayish white |

Each of the test samples and the comparison was heated for 3 h at three different temperatures, 200° C., 300° C. and 450° C., so as to examine the changes in color and their antimicrobial efficacy. In Runs 1 and 2, no structural abnormality occurred in S-2 and S-4 upon heat treatment under the conditions described above. The color of the white powders remained unchanged, demonstrating the high heat resistance of S-2 and S-4. In Run 3, the blue powder of S-7 was used and it did not experience any noticeable change of color upon heat treatment. In Run 5, the known antimicrobial zeolite O-3 was used and it remained white, experiencing no appreciable change of color, when heated at 200° C. for 3 h. However, under more hostile conditions (300° C. × 3 h and 450° C. × 3 h), the color of O-3 turned grayish white. In Run 4, S-8 containing a smaller amount of silver was used and subjected to the heat resistance test under the aforementioned conditions. No abnormality occurred upon heating.

After heating at 450° C. for 3 h, S-2 and S-4 were subjected to an inhibition zone formation test with *Staphylococcus aureus* and the formation of an inhibition zone was verified. Similarly, S-7 was subjected to an inhibition zone formation test with *Bacillus subtilis* after heating at 450° C. for 3 h and the formation of an inhibition zone was verified. After heating at 450° C. for 3 h, the MIC of S-2 was determined using *Escherichia coli* and *Staphylococcus aureus;* the results were 7.8 ppm and 15.6 ppm, respectively. Comparing those results with the data shown in Table 5, one can readily see that the antimicrobial compositions of the present invention had such high heat stability that their efficacy did not deteriorate upon heat treatment.

The antimicrobial composition of the present invention which has an antimicrobial layer on the surfaces of pores in a silica gel matrix is totally composed of inorganic matter and, in addition, the antimicrobial layer forms a coating over the skeletal silica gel, which imparts enhanced heat resistance to the composition. Further, the contents of sodium and other alkali metals in the composition are reduced to such a low level that any adverse effect that may be caused on the composition by the reaction products of alkali metals during heating will be effectively blocked. These factors contribute to the remarkably improved heat resistance and weatherproofness of the antimicrobial composition of the present invention.

EXAMPLES 6-8

These examples relate to a weatherproofness (lightfastness) test conducted on the antimicrobial composition of the present invention. Sample S-2 was used in Example 6, and the dried powders of samples S-7 and S-8 were used in Examples 7 and 8, respectively. Each of these three samples of the antimicrobial composition of the present invention was press-formed into a disk-shaped test piece (diameter, 30 mm; thickness, ca. 2.5 mm).

As comparative samples, the dried fine powders of a silver-containing antimicrobial zeolite O-4 (NaAgZ; Ag=5.31%; Z=Type A zeolite matrix; $D_{av}$=3.4 μm) and a copper-containing zeolite O-5 (NaCuZ; Cu=2.18%; Z=Type A zeolite matrix; $D_{av}$=3.6 pm) were used. Each of these comparative samples was also press-formed into a disk-shaped test piece (diameter, 30 mm; thickness, ca. 2.5 mm).

The antimicrobial compositions of the present invention prepared by the method already described above and the comparative antimicrobial zeolites were exposed to sunlight for 2 months under the same conditions and $\Delta E_{ab^*}$ was determined for each sample on the basis of $L^*$, $a^*$ and $b^*$ measurements conducted before and after the exposure [for calculation of $\Delta E_{ab^*}$, see CIE 1976 $L^*a^*b^*$ standard colorimetric system [JIS Z8729 (980)]; $\Delta E_{ab^*} = ((\Delta L^*)^2 + (\Delta a^*)^2, (\Delta b^*)^2)^{\frac{1}{2}}$]. The results of measurements are described in Table 14 below.

TABLE 14

| Example | Weatherproofness Test Sample | $\Delta E_{ab}^*$ |
|---|---|---|
| Example 6 | S-2 (Ag = 5.20%) | 2.51 |
| Comparative Test 1 | O-4 (Ag = 5.31% | 21.5 |
| Example 7 | S-7 (Cu = 2.04%) | 2.43 |
| Comparative Test 2 | O-5 (Cu = 2.18%) | 10.4 |
| Example 8 | S-8 (Ag = 1.11%) | 1.36 |

Before exposure to sunlight, S-2 had an $L^*$ value of 98.1, an $a^*$ value of −0.9, and a $b^*$ value of −1.7. After the exposure, the respective values were 97.6, 0.2 and 0.5. On the basis of these values, $\Delta E_{ab^*}$ was calculated to be 2.51 as listed in Table 14. In the exposure test (Comparative Test 1) on antimicrobial zeolite O-4 (Ag=5.31%), $\Delta E_{ab^*}$ was 21.5 (before exposure: $L^*$=98.5; $a^*$=−1.1; $b^*$=−4.4; after exposure $L^*$=78.8; $a^*$=2.9; $b^*$=3.2). Comparing the $\Delta E_{ab^*}$ values of S-2 and O-4, one can readily see that S-2, the antimicrobial composition of the present invention, is more weatherproof (lightfast) than O-4, the known antimicrobial zeolite. Sample S-8 had $\Delta E_{ab^*}$ of 1.35, demonstrating its high weatherproofness.

In Example 7, S-7 (Cu=2.04%) was used as another sample of the antimicrobial composition of the present invention. When S-7 was exposed to sunlight for 2 months, its $\Delta E_{ab^*}$ value was calculated to be 2.43 as shown in Table 14. In Comparative Test 2, O-5 (Cu=2.18%) was used as another known antimicrobial zeolite. When O-5 was exposed to sunlight for 2 months, its $\Delta E_{ab^*}$ value was calculated to be 10.4. Comparing the $\Delta E_{ab^*}$ values of S-7 and O-5, one can readily see that S-7, the antimicrobial composition of the present invention, is more weatherproof (lightfast) than O-5.

The silver content was nearly equal in S-2 and O-4 but the former was more weatherproof than the latter. This may be explained as follows: first, the silver present in the antimicrobial layer of the silica gel based antimicrobial composition of the present invention is protected from light by the shielding action of silica, which would help preventing the occurrence of color change due to the photochemical reaction of silver; second, in the antimicrobial composition of the present invention, sodium is fixed in the antimicrobial layer by ionic bonding and its content is very small, 1.23% in sample S-2 and 0.90% in S-7; upon exposure to sunlight, sodium will undergo chemical reaction to form an alkali, which reacts with part of the antimicrobial metal such as silver or copper to produce a hydroxide, a basic salt, an oxide, etc., thereby causing a change in the color of the antimicrobial composition, but because of the ionic bonding of sodium which is present in very small amounts in the antimicrobial composition of the present invention, such change of color by the mechanism described above would be effectively reduced.

Compared to the antimicrobial composition of the present invention, O-4 and O-5 contained sodium in extremely large amounts. The Ag content of O-4 was 5.31% (on an anhydrous basis), which is equivalent to saying that the ion-exchangeable Na+ in type A zeolite, $Na_{12}[(AlO_2)_{12}(SiO_2)_{12}]$, was ion-exchanged with Ag+ for only ca. 7% in terms of silver substitution (percent exchange); in other words, the greater part of sodium remained in the antimicrobial zeolite, presumably in an amount of ca. 14%. In the presence of such excess sodium in the antimicrobial zeolite, exposure to sunlight will initiate a chemical reaction in which sodium forms an alkali that reacts with the antimicrobial metal Ag to produce an impurity that is detrimental to weatherproofness and, at the same time, the silver will undergo photochemical reaction, causing the weatherproofness of the antimicrobial zeolite to deteriorate upon prolonged exposure to sunlight.

EXAMPLES 9-12

These examples relate to the evaluation of the antimicrobial efficacy of antimicrobial polymer compositions.

Samples shaped into a plate, a film or a sheet were tested for their antimicrobial efficacy by the spray method, whereas samples in a fibrous form (monofilamentous) were tested for their antimicrobial efficacy by the already-described shake flask method. For the spray method, suspensions of bacterial and fungal cells were prepared in the manner already described above.

The antimicrobial activity test by the spray method comprised the following: the surface of a test piece (50×50×ca. 1.5 mm except for a film which was 30 μm thick) cleaned with alcohol-impregnated adsorbent wadding was sprayed with a predetermined amount of cell suspension and stored at 35° C. for a predetermined time. Before measurement, the cells on the test piece were washed off and the number of cells in the washings was counted.

EXAMPLE 9

This example relates to the preparation of a shaped polyvinylidene chloride (PVDC) containing the antimicrobial composition of the present invention having the antimicrobial metal silver supported on an antimicrobial layer formed on the surfaces of pores in a silica gel matrix. The example also relates to the evaluation of the antimicrobial efficacy of that shaped polymer.

Sample S-2 was pulverized with a jet mill into fine particles having an average size ($D_{av}$) of 8 μm. By heating at 200° C. under vacuum, the powder was dehydrated to a water content of 2.6% and less. The dried fine powder was added to PVDC in an amount of 2.0% or 3.0% on an anhydrous basis. Each of the mixtures was heated to ca. 180° C., mixed further at the same temperature to homogeneity, and subsequently press formed at ca. 23 kg/cm$^2$G into a shape measuring ca. 100×100 mm (ca. 1.5 min thick). The shapes were cut to a size of ca. 50×50 min (ca. 1.5 mm thick) to prepare two test specimens (PVDC-1 and PVDC-2). As a comparison, a shaped PVDC (ca. 100×100 mm; ca. 1.5 mm thick) for use in a blank test was prepared without incorporating any antimicrobial composition. The PVDC was cut to a small test specimen (PVDC-BL; ca. 50×50 mm; ca. 1.5 mm thick).

Using the three test specimens, an antimicrobial efficacy test was performed by the spray method and the results are shown in Table 15. Specimens PVDC-1 and PVDC-2 which were PVDC polymer compositions containing the antimicrobial composition of the present invention in respective amounts of 2.0% and 3.0% proved effective in killing *Bacillus subtilis*. After the passage of 2 h, the number of viable *B. subtilis* cells was zero, indicating they had been completely killed.

TABLE 15

Antimicrobial Activity Test by the Spray Method (Example 9)

| Specimen designation | S-2 content of polymer | Micro-organism | Time-dependent change in cell count (No. of viable cells per specimen) 0 | 2 | 5 (h) |
|---|---|---|---|---|---|
| PVDC-1 | 2.0% | Bacillus subtilis | 6.7 × 10$^6$ | 0 | 0 |
| PVDC-2 | 3.0% | Bacillus subtilis | 6.7 × 10$^6$ | 0 | 0 |
| PVDC-BL | — | Bacillus subtilis | 6.7 × 10$^6$ | 6.5 × 10$^6$ | 2.1 × 10$^6$ |
| PVDC-2 | 3.0% | Aspergillus niger | 7.1 × 10$^6$ | 3.8 × 10 | 0 |
| PVDC-BL | — | Aspergillus niger | 7.1 × 10$^6$ | 7.0 × 10$^6$ | 6.8 × 10$^6$ |

As Table 15 shows, the specimen PVDC-BL for blank test had no antimicrobial efficacy. In the test for efficacy against fungus *Aspergillus niger*, PVDC-2 reduced the number of viable cells to 3.8×10 per specimen after the passage of 2 h and this was equivalent to a death rate of 99.999%, with an extremely small number of cells living alive. After the passage of 5 h, all *A. niger* were found to be dead. On the other hand, PVDC-BL or the specimen for blank test did not show any antifungal activity.

The results of the antimicrobial efficacy test described above clearly show that the antimicrobial polymer composition of the present invention has excellent antimicrobial or microbicidal activity.

EXAMPLE 10

This example relates to the preparation of a shaped polyvinyl chloride (PVC) containing the antimicrobial composition of the present invention having the antimicrobial metal silver supported on an antimicrobial layer formed on the surfaces of pores in a silica gel matrix. The example also relates to the evaluation of the antimicrobial efficacy of that shaped polymer.

Sample S-2 was pulverized with a jet mill into fine particles having an average size ($D_{av}$) of 8 μm. By heating at 220° C. under vacuum, the powder was dehydrated to a water content of 1.5% and less. The dried fine powder was added to PVC and the mixture was shaped to form a PVC sheet by the following procedure. First, 50 parts of a plasticizer DOP was added to 100 parts of PVC. ("Nippolit SL" of general purpose grade of Chisso Corporation; degree of polymerization, 1000); after adding a stabilizer and a gelation accelerator in small amounts, the previously prepared fine powder of antimicrobial composition was added in such an amount that it would assume 1.9% of the mixture (the resulting specimen designated PVC-1) or 3.1% of the mixture (the resulting specimen designated PVC-2). The mixtures were then heated at 140°–150° C. and homogenized by kneading on mixing rolls. The homogenized mixtures were shaped into sheets of a thickness of ca. 1.5 mm.

The PVC sheets were cut to form specimens for antimicrobial test (ca. 50×50 mm; 1.5 mm thick). Using those test specimens, an antimicrobial activity test was performed by the spray method. As a comparison, a PVC sheet for use in a blank test was prepared by the same method as described above except that it did not contain any antimicrobial composition. The sheet was cut to a smaller test specimen (PVC-BL; ca. 50×50 mm; 1.5 mm thick) which was also subjected to an antimicrobial activity test by the spray method. The results are shown in Table 16 below.

TABLE 16

Antimicrobial Efficacy Test by the Spray Method (Example 10)

| Specimen designation | S-2 content of polymer | Micro-organism | Time-dependent change in cell count (No. of viable cells per specimen) 0 | 3 | 6 (h) |
|---|---|---|---|---|---|
| PVC-1 | 1.9% | Staphylococcus aureus | 7.4 × 10$^6$ | 0 | 0 |
| PVC-2 | 3.1% | Staphylococcus aureus | 7.4 × 10$^6$ | 0 | 0 |
| PVC-BL | — | Staphylococcus aureus | 7.4 × 10$^6$ | 7.1 × 10$^6$ | 6.9 × 10$^6$ |

As Table 16 shows, specimens PVC-1 and PVC-2 that contained the antimicrobial composition of the present invention in respective amounts of 1.9% and 3.1% could reduce the number of viable *Staphylococcus aureus* cells to zero after the passage of 3 h, demonstrating total annihilation of the microorganism. On the other hand, PVC-BL or the specimen for blank test did not show any efficacy against *Staphylococcus aureus*.

The results of the antimicrobial efficacy test described above clearly show that the PVC polymer composition containing the antimicrobial composition of the present invention has a significant and hence preferred microbicidal activity.

EXAMPLE 11

This invention relates to the preparation of a PP (polypropylene) film containing the antimicrobial composition of the present invention that has both silver and zinc supported as antimicrobial metals on an antimicrobial layer formed on the surfaces of pores in a silica gel matrix.

The dried product of sample S-4 was ground with a pulverizer into fine particles having an average size ($D_{av}$ of 6 μm. By heating at ca. 220° C. under vacuum, the powder was dehydrated to a water content of 1.5% and less. The dried fine powder was mixed with PP (A 414 of Chisso Corporation) in such an amount that the former would assume 1.5% of the mixture (the resulting specimen designated PP-1) or 2.0% of the mixture (the resulting specimen designated PP-2). The mixtures were then shaped into films 30μm thick by inflation molding with the cylinder and die outlet being held at temperatures of 210°–220° C. and ca. 220° C., respectively, and with the screw rotating at 25 rpm. The resulting PP films were cut into small test pieces (PP-1 and PP-2 each measuring ca. 50 mm × 50 mm × 30 μm), which were subjected to an antimicrobial activity test. As a comparison, a PP film (30 μm thick) containing no antimicrobial composition was prepared as already described for use in a blank test. This film was cut into small Lest pieces (ca. 50 mm × 50 mm × 30 pm), designated PP-BL, and subjected to an antimicrobial test. The results are shown in Table 17 below.

TABLE 17
Antimicrobial Activity Test by the Spray Method (Example 11)

| Test sample | Content of S-4 in polymer composition (%) | Micro-organism | Time-dependent change in cell count (No. of viable cells per sample) | | |
|---|---|---|---|---|---|
| | | | 0 | 3 | 6 (h) |
| PP-1 | 1.5 | Staphyl-ococcus aureus | 5.3 × 10⁶ | 0 | 0 |
| PP-2 | 2.0 | Staphyl-ococcus aureus | 5.3 × 10⁶ | 0 | 0 |
| PP-BL | — | Staphyl-ococcus aureus | 5.3 × 10⁶ | 5.1 × 10⁶ | 4.3 × 10⁶ |

When PP-1 and PP-2 films containing the antimicrobial composition of the present invention respective amounts of 1.5% and 2% were used, the cell count of *Staphylococcus aureus* was zero at 3 hours, indicating the strong bactericidal activity of these samples. On the other hand, PP-BL film as the blank test sample was not at all effective against Staphylococcus aureus. These results clearly show that the PP polymer composition in film form which contained the antimicrobial composition of the present invention exhibits remarkable microbicidal activity.

EXAMPLE 12

This example relates to the preparation of HDPE (high-density polyethylene) monofilaments (fibrous) containing antimicrobial compositions of the present invention that have silver and copper retained as antimicrobial metals on the antimicrobial layer formed on the surfaces of pores in a silica gel matrix. The example also relates to the evaluation of the antimicrobial activity of those monofilaments.

A mixture of S-1 are S-7 was used as a sample. An antimicrobial composition containing silver as an antimicrobial metal and an antimicrobial composition containing copper as an antimicrobial metal were individually dried and ground with a jet mill to fine articles having a $D_{av}$ of 5.6 μm (in the former case) or 6.8 μm (in the latter case). Both fine powders were heated at 220° C. under vacuum to a water content of 1.7% and below. Each of the dried fine powders of two antimicrobial compositions was mixed with HDPE in such an amount that S-1 and S-7 would each assume 0.8% of the polymer composition (HDPE-1) and 1.5% of the polymer composition (HDPE-2). The mixtures were then shaped into antimicrobial HDPE monofilaments by extrusion molding under the following conditions: temperature, 220°±5° C.; pressure, ca. 100 kg/cm²G; residence time, 10–14 min; throughput, 1.5 kg/h; screw rotating speed, 20 rpm; length (L) to diameter (D) ratio of screw, L/D≈25. The monofilaments were drawn at a ratio of ca. 10 to a fineness of ca. 400 denier. HDPE monofilaments containing no antimicrobial agent were also prepared in accordance with the manner described above (HDPE-BL).

The monofilaments prepared as described above had satisfactory physical properties and exhibited adequate strength. Using those monofilaments, a test was conducted to evaluate their antimicrobial activity by the shake flask (SF) method already described herein. The results are shown in Table 18 below.

TABLE 18
Antimicrobial Activity Test by the SF Method (Example 12)

| Test sample | Content of the anti-microbial compositions in polymer composition | Micro-organism | Time-dependent change in cell count (No. of viable cells per sample | | |
|---|---|---|---|---|---|
| | | | 0 | 2 | 8 (h) |
| HDPE-1 | 0.8%* | Escher-ichia coli | 4.8 × 10⁶ | 0 | 0 |
| HDPE-2 | 1.5%** | Escher-ichia coli | 4.8 × 10⁶ | 0 | 0 |
| HDPE-BL | — | Escher-ichia coli | 4.8 × 10⁶ | 4.5 × 10⁶ | 4.1 × 10⁶ |
| HDPE-2 | 1.5%** | Aspergil-lus niger | 7.2 × 10⁶ | 3.9 × 10 | 0 |
| HDPE-BL | — | Aspergil-lus niger | 7.2 × 10⁶ | 7.2 × 10⁶ | 6.9 × 10⁶ |

*Each of the S-1 and S-7 contents in the polymer composition was 0.8%.
**Each of the S-1 and S-7 contents in the polymer composition was 1.5%.

When HDPE-1 and HDPE-2 monofilaments were used, the cell count of bacterial *Escherichia coli* was zero at 2 hours, indicating the strong bactericidal activity of these samples. On the other hand, HDPE-BL as the blank test sample containing no antimicrobial composition was not at all effective against *Escherichia coli*. When HDPE-2 monofilaments was used, the cell count of fungal *Aspergillus niger* was 3.9×10 cells per ml at 2 hours, which was equivalent to a death rate of at least 99.99%. When 8 hours passed, all cells were found dead. On the other hand, HDPEBL monofilaments as the blank test sample were not at all effective against *Aspergillus niger*. These results clearly show that the HDPE monofilaments containing the antimicrobial composition of the present invention exhibit strong microbicidal action.

EXAMPLE 13

This example relates to a weathering (lightfastness) test conducted on shaped, antimicrobial polypropylene parts containing an antimicrobial composition of the present invention.

Samples S-2 and O-4 were individually heated at ca. 220° C. under vacuum to a water content of 2% and below. The thus treated antimicrobial powders and a polypropylene (PP) resin in powder form were mixed in predetermined proportions (see Table 19 below). The mixtures were held in a molten state at ca. 200° C. until homogeneity and press formed at ca. 23 kg/cm$^2$G into plates (100×100×1.5 mm). The thus shaped antimicrobial PP parts were cut to two test pieces PP-3 and PP-4 each measuring 50×50×1.5 mm, which were subjected to a weathering test by the following procedure. The two PP samples each having an antimicrobial content of 0.5% were exposed to sunlight for 2 months under the same conditions and, in the same manner as in the test described in Table 14, $\Delta E_{ab}*$ was calculated from the L*, a* and b* values of each sample as measured before and after the exposure. The results are described in Table 19.

TABLE 19

Weathering Test (Example 13)

| Test sample | Antimicrobial agent and amount of its addition to PP | $\Delta E_{ab}*$ |
|---|---|---|
| PP-3 | S-2 (Ag = 5.20%), 0.5% | 1.3 |
| PP-4 (comparison) | O-4 (Ag = 5.31%), 0.5% | 9.8 |

It is clear from Table 19 that the shaped PP part (PP-3) containing 0.5% of the antimicrobial composition of the present invention was much more weatherproof than the shaped PP part (PP-4) containing 0.5% of the known antimicrobial zeolite O-4. As already mentioned, the silver present in the antimicrobial layer on the silica gel based antimicrobial composition of the present invention is isolated from light by the silica gel matrix. This antimicrobial composition of the present invention is uniformly dispersed in PP so that the change in the color of the shaped PP part that would otherwise occur on account of the photochemical reaction of silver upon exposure to sunlight can be prevented as much as possible. Further, the sodium content of S-2 is very small (1.23%) so that the chemical reaction of sodium in the PP sample containing the antimicrobial composition of the present invention is sufficiently inhibited to prevent deterioration in the weatherproofness of the shaped PP part. On the other hand, the shaped PP part containing the known antimicrobial zeolite O-4 (NaAgZ) is highly susceptible to light and experiences a great change in color after exposure to light for 2 months.

In summary, the antimicrobial composition of the present invention is based on a silica gel, which makes it entirely different from known inorganic antimicrobial zeolites in terms of chemical composition and skeletal structure. As already mentioned hereinabove, the antimicrobial layer of the composition of the present invention is formed on the surfaces of large-diameter pores in the silica gel matrix and is therefore very stable. The antimicrobial metal or metals in this antimicrobial layer are uniformly distributed and non-antimicrobial metals such as alkali metal are present in only small amounts in that layer. As already mentioned, this antimicrobial layer is covered with silica which is the major component of the matrix. On the other hand, the pores in the known antimicrobial zeolites are smaller in size than those i-n the antimicrobial composition of the present invention (for example, the pore size of type A and X zeolite matrices is 4 Å and 10 Å, respectively). Therefore, the antimicrobial metal generated upon dissociation of antimicrobial agent will diffuse through pores much more rapidly in the antimicrobial composition of the present invention than in the antimicrobial zeolite and, considering the area of contact between the antimicrobial agent and microorganism, the composition of the present invention is much more advantageous than the known antimicrobial agents. The active surface of the antimicrobial composition of the present invention is capable of adsorbing more bacteria and fungi than known antimicrobial zeolites and, hence, the composition exhibits a stronger antimicrobial or microbicidal activity. As demonstrated in the various tests described above, this fact was positively verified by the outstanding antimicrobial efficacy of the composition that greatly surpassed the effectiveness of the antimicrobial zeolites. Another feature of the composition of the present invention is that it needs to contain a smaller amount of antimicrobial metal or metals in order to achieve the same efficacy as known antimicrobial zeolites. These differences in efficacy between the two types of antimicrobial agent are ascribable to the essential difference in the structure of matrix. Stated more specifically, antimicrobial metal ions generated by dissociation of an antimicrobial zeolite also diffuse through macropores or micropores in the zeolite; however, the diameter of the micropores is so small that the rate of diffusion through pores is reduced to have a substantial amount of antimicrobial metal ion left unavailable for exhibiting the intended antimicrobial effect. This would probably cause the aforementioned differences in efficacy between the antimicrobial composition of the present invention and known antimicrobial zeolites.

For the reasons stated above, the "effective availability" for microorganisms (bacteria and fungi) of the antimicrobial composition of the present invention is extremely higher than that of known antimicrobial zeolites, as supported by the test data shown in Examples of the present invention. In addition, the antimicrobial composition of the present invention is much more heat-resistant and weatherproof than known zeolites and this is probably because the antimicrobial layer of the composition is "coated" with excess silica. Another possible reason is that the content of alkali metal in the antimicrobial layer is reduced to such a low level that its potential adverse effects on weatherproofness are held at minimum.

The silica-gel based heat-resistant and weatherproof composition of the present invention has the following principal features or advantages.

(1) The composition is totally composed of inorganic matter and hence it is structurally more stable than organic antimicrobial agents, has a smaller vapor pressure (i.e., involatile) and is more heat-resistant. Further, the composition is odorless, chemically stable, has little toxicity and is highly safe to the human body.

(2) Having the unique essential elements described hereinabove, the antimicrobial composition of the present invention is by far superior in heat resistance and weatherproofness over known inorganic antimicrobial agents such as antimicrobial zeolites.

(3) The antimicrobial composition of the present invention exhibits an outstanding antimicrobial or microbicidal activity compared to known inorganic antimicrobial agents and it has a broader antimicrobial spectrum. It needs to be used in a smaller amount than known inorganic antimicrobial agents to exhibit excellent efficacy against both bacteria and fungi and yet its antimicrobial or microbicidal action is sustained over a prolonged period. The microbicidal speed of the composition is incomparably higher than that of known antimicrobial zeolites.

(4) The ability of the composition of the present invention to kill common bacteria is surprisingly great compared to known inorganic antimicrobial agents. The ability of the composition to kill fungi is also surprisingly great compared to known antifungal agents.

(5) The composition of the present invention has an extremely higher bactericidal speed than known inorganic bactericides. The significant difference in bactericidal speed between the two types of agents is based on the essential difference in the matrix structure.

(6) The composition of the present invention is slightly soluble in water. The antimicrobial or microbicidal layer formed on the surfaces of pores in the silica gel matrix binds stably to the matrix gel and is of course slightly soluble in water. This layer permits antimicrobial metal ions to be released in a preferred slow manner. Further, the released antimicrobial metal ions diffuse through the pores in the gel matrix at such a high speed that the reaction between Microorganisms and antimicrobial metal ions can be performed in the ideal fashion.

(7) The antimicrobial composition of the present invention exhibits antimicrobial or microbicidal action on various microorganisms present in a gas, a liquid and a solid phase.

(8) The particle size of the composition can be adjusted to any desired value. Further, it will not undergo any disintegration into fines during use. Therefore, the composition is suitable for use in a broad range of applications.

(9) The composition has such good dispersibility that it can be easily added to or mixed with various polymers. In addition, almost all kinds of Polymers can be rendered antimicrobial by incorporating the necessary amounts of the composition without causing deterioration of the physical properties of those polymers.

(10) The composition itself has high heat resistance and weatherability, so antimicrobial polymers prepared by rendering polymers antimicrobial through the use of this composition will experience only negligible time-dependent changes in its physical properties. The thus prepared antimicrobial polymer of the present invention not only exhibits excellent efficacy against common bacteria and fungi over a prolonged period but also achieves great antialgal action. (11) As already mentioned above, the composition has little toxicity and is highly safe to the human body. Hence, the antimicrobial polymer containing the composition is also highly safe to the human body.

(12) The polymer treated by addition or mixing of the composition is rendered antimicrobial per se; at the same time, the thus prepared antimicrobial polymer will exhibit desired antimicrobial effects on microorganisms that may be present in a gas or a liquid phase in contact with said polymer.

(13) Having superior antimicrobial action over known inorganic antimicrobial agents such as antimicrobial zeolites, the composition of the present invention need be used in a smaller amount to achieve comparable levels of effectiveness when it is added to or mixed with polymers to prepare antimicrobial polymers.

What is claimed is:

1. An antimicrobial composition composed of silica gel having a metal aluminosilicate layer on its surface area characterized in that said silica gel has a pore volume of at least 0.3 cm$^3$/g and a specific surface area of at least 100 m$^3$/g, and in that said layer is stably bonded on the surface of the matrix of silica gel and on the active surfaces of the pores in the silica gel, wherein said metal aluminosilicate coat layer is characterized in that antimicrobial metal completely or partially substitutes for the ion-exchangeable metal (M) in an aluminosilicate solid coating layer represented by the formula $$xM_{2/n}O.Al_2O_3.ySiO_2.ZH_2O$$

where x and y represent the numbers of molecules of the metal oxide and silicon dioxide, respectively; M is an ion-exchangeable metal; n is the atomic valence of M; and z is the number of molecules of water, said ion-exchangeable metal having been selected from the group consisting of lithium, sodium, potassium and mixtures thereof in an amount of up to 2.57 mmol per gram of said composition on an anhydrous basis and wherein said antimicrobial metal is selected from the group consisting of silver, silver and copper, silver and zinc, silver and mercury, silver and tin, silver and lead, silver and bismuth, silver and cadmium, silver and chromium, and mixtures thereof; and wherein said composition is stable at less than 500° C. and does not show deterioration of antimicrobial ability in a temperature range of 100° C.-500° C.

2. A polymer composition that comprises the antimicrobial composition of claim 1 and a halogenated or non-halogenated organic polymer wherein the amount of said antimicrobial composition is in the range of 0.01-25 wt % of the polymer composition.

3. A polymer composition that comprises the antimicrobial composition of claim 1 and a polymer selected from the group consisting of polyvinylidene chloride, polyvinyl chloride, polypropylene, and high-density polyethylene wherein the amount of said antimicrobial composition is in the range of 0.01-25 wt % of the total composition.

4. An antimicrobial polymer composition according to claim 3 wherein the amount of the antimicrobial composition is in the range of 0.01-25 wt % of the total composition.

5. A process for producing the composition of claim 1, which process comprises the steps of:
1) treating a silica gel with an alkali solution and an ion-exchangeable metal aluminate solution to obtain a reaction product that has a non-antimicrobial aluminosilicate layer stably bonded on the surface of the matrix of the silica gel and on the active surfaces of pores in the silica gel, the ion-exchangeable metals in said layer being an alkali metal selected from the group consisting of lithium, sodium, potassium and mixtures thereof and being present in an amount of up to 2.6 mmol per gram of the reaction product; and
2) subjecting the ion-exchangeable metals on said non-antimicrobial layer to ion-exchange with antimicrobial metal selected from a group consisting of silver, silver and copper, silver and zinc, silver and mercury, silver and tin, silver and lead, silver and bismuth, silver and cadmium, silver and chromium, and mixtures thereof.

* * * * *